(12) United States Patent
Campbell

(10) Patent No.: US 12,117,534 B2
(45) Date of Patent: Oct. 15, 2024

(54) LOCATION DETERMINATION FOR SUBSURFACE COMMUNICATION DEVICE

(71) Applicant: GroGuru, Inc., San Diego, CA (US)

(72) Inventor: Jeffrey E. Campbell, Boise, ID (US)

(73) Assignee: GroGuru, Inc., San Diego, CA (US)

( * ) Notice: Subject to any disclaimer, the term of this patent is extended or adjusted under 35 U.S.C. 154(b) by 584 days.

(21) Appl. No.: 17/598,646

(22) PCT Filed: Mar. 28, 2020

(86) PCT No.: PCT/US2020/025591
§ 371 (c)(1),
(2) Date: Sep. 27, 2021

(87) PCT Pub. No.: WO2020/198727
PCT Pub. Date: Oct. 1, 2020

(65) Prior Publication Data
US 2022/0187474 A1    Jun. 16, 2022

Related U.S. Application Data

(60) Provisional application No. 62/825,719, filed on Mar. 28, 2019.

(51) Int. Cl.
*G01S 19/07* (2010.01)
*G08C 17/02* (2006.01)
*H04W 4/029* (2018.01)

(52) U.S. Cl.
CPC ............ *G01S 19/073* (2019.08); *G08C 17/02* (2013.01); *H04W 4/029* (2018.02)

(58) Field of Classification Search
CPC ...... G01S 19/073; G08C 17/02; H04W 4/029; H04W 4/38; H04B 5/26; H04B 5/73;
(Continued)

(56) References Cited

U.S. PATENT DOCUMENTS 7,755,422 B2 * 7/2010 Schell ...................... H03C 5/00
330/297
7,796,943 B2    9/2010 Levan
(Continued)

OTHER PUBLICATIONS

International Search Report and Written Opinion issued for International Patent Application No. PCT/US2020/025591 dated Jun. 15, 2020.

*Primary Examiner* — Alvaro E Fortich

(57) ABSTRACT

A sensor location method includes placing an environmental sensor within an electromagnetic-absorbing material. The sensor is configured to sense a condition of the material and output sensor data representing the condition. The method includes providing a modulator configured to encode the sensor data onto a carrier at a carrier frequency. The method includes providing an amplifier, including a switch and a load network, in communication with a multi-turn coil. The switch can transition between on and off states. The network is coupled to the switch and the first multi-turn coil and includes a terminal that receives a voltage. The network is tunable to form a resonant circuit at the carrier frequency. The method includes generating a beacon signal whose amplitude is adjustable. The method includes receiving the beacon by a receiver outside of the material, measuring the received beacon amplitude, and determining the sensor location based upon the measured amplitude.

16 Claims, 16 Drawing Sheets

(58) Field of Classification Search
CPC ........ H04B 5/77; H04Q 2209/86; H04Q 9/00; H04Q 2209/40; G01N 33/24
See application file for complete search history.

(56) References Cited

U.S. PATENT DOCUMENTS

| | | |
|---|---|---|
| 7,884,620 B2 | 2/2011 | Campbell |
| 8,571,135 B2 | 10/2013 | Sorrells et al. |
| 9,046,461 B1 | 6/2015 | Sohrabi et al. |
| 2008/0171512 A1* | 7/2008 | Jack ................. H04B 5/48 455/41.1 |
| 2009/0170433 A1* | 7/2009 | Rhodes ............... H04B 5/00 455/41.1 |
| 2013/0221911 A1* | 8/2013 | Low ................. H04B 5/26 320/108 |
| 2017/0269016 A1* | 9/2017 | Anjum ............... G01W 1/02 |

\* cited by examiner

LOCATION DETERMINATION FOR SUBSURFACE COMMUNICATION DEVICE

CROSS-REFERENCE TO RELATED APPLICATIONS

This application is a U.S. national stage application of International Patent Application No. PCT/US2020/025591, filed Mar. 28, 2020, and entitled "Location Determination For Subsurface Communication Device." International Application No. PCT/US2020/025591 claims the benefit of U.S. Provisional Patent Application No. 62/825,719, filed Mar. 28, 2019, and entitled "Location Determination For Subsurface Communication Device." The entirety of each of these applications is incorporated by reference.

BACKGROUND

Sensing environmental conditions within an electromagnetic-absorbing material (e.g., soil, concrete, water) is desired in a variety of applications, including agriculture. While various types of sensors are available for measuring environmental conditions within a material, communicating data from the sensors to outside the material can be challenging. Using a wired connection can be successful, but wires are undesirable or impractical in many applications. For example, in agriculture applications, wires are easily broken or damaged by rodent activity or tilling/harvesting operations. In other applications, use of wired connections is undesirable due to the potential for vandalism, appearance, or other reasons. While the use of wireless connections has been proposed to alleviate some of these problems, numerous challenges have prevented practical commercial application. These challenges can include: inadequate communications range due to the attenuation of propagating electromagnetic waves (particularly in an electromagnetic-absorbing material), unreliable operation due to changes in electromagnetic characteristics of the material, large equipment/antenna sizes that are incompatible with easy installation/removal of buried sensors, and excessive power consumption incompatible with long-term or battery-powered operation.

SUMMARY

Systems and methods are described for obtaining environmental readings from within an electromagnetic-absorbing material. In some embodiments, a system may include an environmental sensor and a modulator coupled to the environmental sensor. The modulator may encode data from the sensor onto a carrier having a carrier frequency between about 9 kHz and about 1705 kHz. The system may also include a switch-mode amplifier powered from a self-contained power supply. The switch-mode amplifier may amplify the carrier which may then be transmitted via a multi-turn coil with a diameter of less than about 0.3 meter. The multi-turn coil may have a reactance at the carrier frequency that may form a part of a frequency-dependent load network coupled to the amplifier to minimize current and voltage during switching transients of the switch-mode amplifier.

In an embodiment, a method of locating a sensor is provided. The method includes placing an environmental sensor within an electromagnetic absorbing material. The environmental sensor can be configured to sense at least one environmental condition of the electromagnetic-absorbing material and to output sensor data representing the at least one environmental condition. The method also includes providing a modulator in communication with the environmental sensor. The modulator can be configured to encode the sensor data onto a carrier at a predetermined carrier frequency. The method additionally includes providing a switch-mode amplifier in communication with the signal output and a first multi-turn coil. The switch mode amplifier includes a first switching device and a load network. The first switching device can be configured to transition between an on state and an off state. The load network is coupled to the first switching device and the load network includes a terminal configured to receive an input voltage and the first multi-turn coil. The inductance and capacitance of the load network can be tunable to form a resonant circuit at the predetermined carrier frequency. The method additionally includes generating, by the first multi-turn coil, a beacon signal. An amplitude of the beacon signal can be adjustable. The method further includes receiving, by a second multi-turn coil of a receiver positioned outside of the electromagnetic-absorbing material, the beacon signal. The method also includes measuring the amplitude of the received beacon signal. The method additionally includes determining a location of the environmental sensor based upon the measured amplitude of the beacon signal.

In an embodiment, generating the beacon signal includes generating a single beacon signal by placing the first switching device in the on position for a predetermined time duration.

In an embodiment, generating the beacon signal includes generating a plurality of beacon signals by transitioning the first switching device between the on state and off state for each beacon signal.

In an embodiment, the amplitude of the beacon signal can be adjusted by changing the magnitude of the input voltage.

In an embodiment, the amplitude of the generated beacon signal can be adjusted by shifting a frequency of the beacon signal with respect to a resonant frequency of the resonant circuit.

In an embodiment, the method can also include receiving, by the first multi-turn coil, a command signal operative to adjust the amplitude of the beacon signal.

In an embodiment, the first multi-turn coil can generate the beacon signal when the first switching device is placed in the on state.

In an embodiment, the method also includes providing a pulse generator in communication with a second switching device, the second switch device being further in communication with the load network. The method further includes generating, by the pulse generator, a beacon pulse. The method additionally includes placing the second switching device in an on state during receipt of the beacon signal. The first multi-turn coil can generate the beacon signal when the second switching device is placed in the on state. The first switching device can be placed in the off state during generation of the beacon pulse and the second beacon signal.

In an embodiment, the method further includes generating a first beacon signal having a first amplitude and a first duration. The method also includes generating a second beacon signal having a second amplitude and a second duration. The method additionally includes generating a third beacon signal having a third amplitude and a third duration. The first amplitude can be greater than the second and third amplitude and the second amplitude can be greater than the third amplitude. The first duration can be less than the second and third durations and the second duration can be less than the third duration.

In an embodiment, an axis of the first multi-turn coil can be oriented orthogonally to a surface of the electromagnetic-absorbing material. The method further includes orienting the receiver such that an axis of the second multi-turn coil is approximately perpendicular to the surface of the electromagnetic-absorbing material. The method also includes moving the receiver with respect to the first multi-turn coil while maintaining an approximately constant distance between the receiver and the surface of the electromagnetic-absorbing material. The method additionally includes identifying the location of the environmental sensor as the location where the amplitude of the third beacon signal is less than a predetermined amplitude threshold and the amplitude of at least one of the first and second beacon signals is greater than or equal to the predetermined amplitude threshold.

In an embodiment, the method also includes determining a distance between the receiver and the environmental sensor based upon the measured amplitude of at least one of the first, second, or third beacon signals.

In an embodiment, the method also includes providing, by an audio or visual device, an indication of the distance between the Receiver and the environmental sensor.

In an embodiment, the predetermined carrier frequency is selected from about 9 kHz to about 1705 kHz.

In an embodiment, the predetermined carrier frequency is selected from about 50 kHz to about 490 kHz.

In an embodiment, the first multi-turn coil can have a diameter of less than 0.3 meter.

In an embodiment, the switch-mode amplifier can be a class-E amplifier.

DESCRIPTION OF DRAWINGS

Features, aspects, and embodiments are described in conjunction with the attached drawings.

DETAILED DESCRIPTION

A detailed description of one or more embodiments is provided below along with accompanying figures. Numerous specific details are set forth in the following description in order to provide a thorough understanding of the invention. These details are provided for the purpose of example and the invention may be practiced according to the claims without some or all of these specific details.

Setup and Configuration

Figure 1:
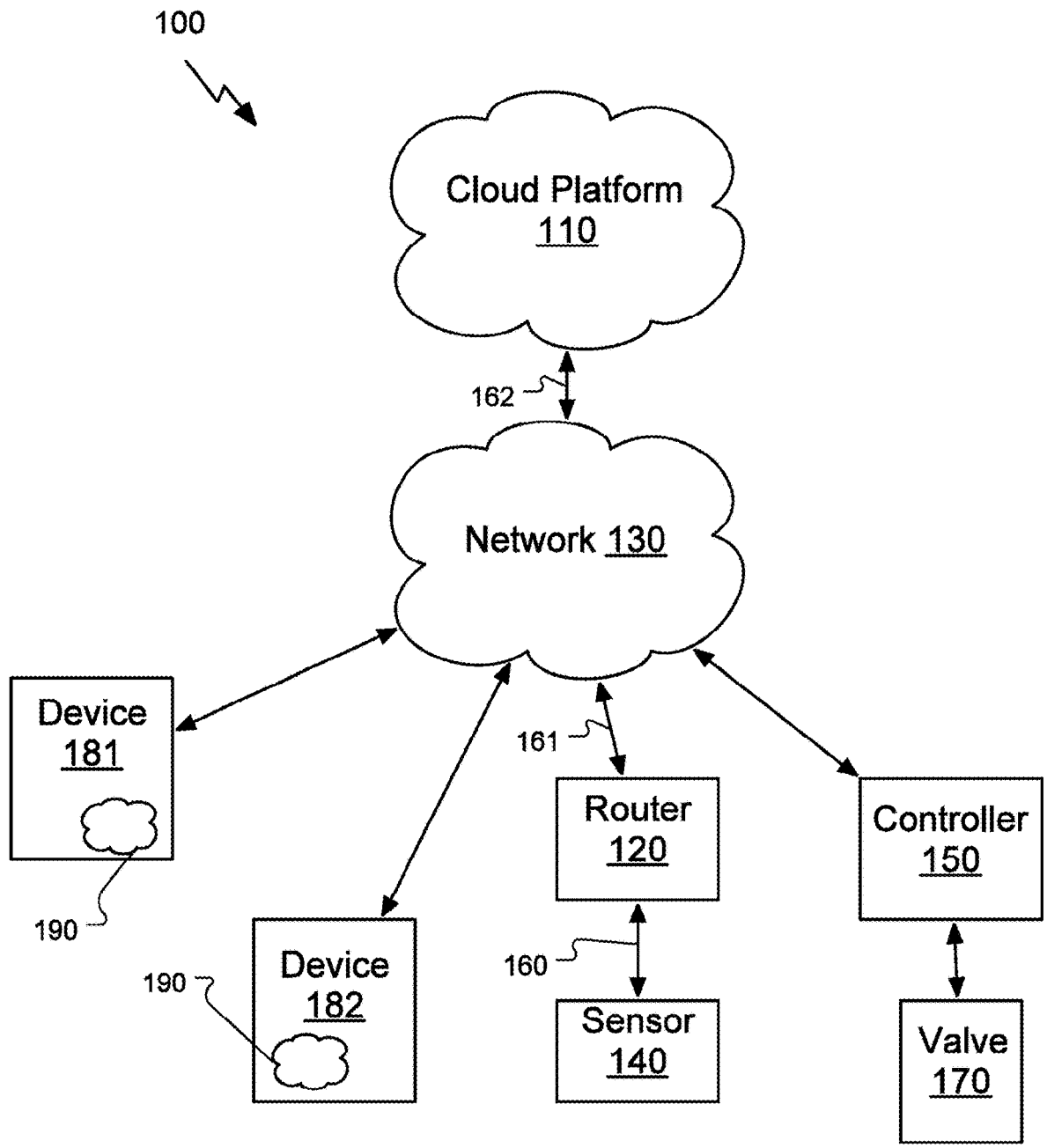
FIG. 1 is a diagram illustrating an embodiment of a system for dynamically collecting, analyzing, and regulating garden parameters.

FIG. 1 is a diagram illustrating an embodiment of a System 100 for dynamically collecting, analyzing, and regulating garden parameters. Although the term "garden" is used throughout, it is to be understood that the systems and methods described herein are applicable to and can be used in any area or location where plants are grown or to be grown, including but not limited to orchards, farms, vineyards, lawns, nurseries, planters, fields, parks, etc. In addition, the systems and methods described herein are applicable to and can be used for other applications where embedded monitoring in a material may be useful, such as monitoring cement curing or water conditions near a dam, under road beds, in a levee, etc. As shown in FIG. 1, in some of the embodiments described herein, System 100 may comprise a Cloud Platform 110, which may communicate with a Router 120 via Network 130. In various embodiments, Network 130 may be the Internet, and can include wireless and wired WANs, LANs, or PANs. In some of the embodiments described herein, Router 120 may also communicate with Sensor 140 or Controller 150. In various embodiments, Router 120 may communicate with Sensor 140 or Controller 150 via a wireless connection. In various embodiments, Router 120 may communicate with Sensor 140 or Controller 150 using a Wi-Fi connection. It is to be understood that in various other embodiments of System 100 not shown in FIG. 1, Router 120 may communicate with any appropriate, required, or desired number (e.g., two or more) of sensors (e.g., Sensor 140) or controllers (e.g., Controller 150). It is also to be understood that Controller 150 is optional and in some embodiments of System 100 not shown in FIG. 1, System 100 may operate without Controller 150. Finally, it is to be understood that, in various embodiments, the functionalities of Sensor 140 and Controller 150 may be integrated into a single hybrid device or apparatus.

In various embodiments, Sensor 140 may be configured to take one or more measurements in order to generate Data 160. For example, in various embodiments, Sensor 140 may be capable of measuring temperature, light, and moisture. Meanwhile, in various embodiments, Data 160 may include at least one real time garden parameter, including but not limited to soil moisture, soil salinity, soil temperature, soil pH, external temperature, external humidity, and light exposure. In various embodiments, Sensor 140 may be configured to take measurements according to a predetermined or to a dynamic schedule or frequency. Furthermore, in various embodiments, Sensor 140 may also be configured to transmit Data 160 to Router 120. In some embodiments, Data 160 may be transmitted to Router 120 in real time. In other embodiments, Data 160 may be transmitted to Router 120 at preset intervals (e.g., hourly, daily, weekly) or at variable intervals, which can change dynamically based on one or more factors such as user input or the frequency of measurements taken by Sensor 140.

In some embodiments, Controller 150 may be configured to control sprinkler Valve 170. In various embodiments, Controller 150 may receive signals from Router 120 that include commands or instructions to open and to close Valve 170. In various embodiments, based on the instructions from Router 120, Controller 150 may then instruct Valve 170 to open or to close. In some embodiments, Valve 170 may be a solenoid valve, a type of valve that is commonly found in various residential and commercial sprinkler systems. In some embodiments, Controller 150 may be particularly well suited to controlling solenoid valves. In some embodiments, Controller 150 may directly cause Valve 170, a solenoid valve, to open and to close by modulating the electric current that controls the valve. Thus, in some embodiments, Controller 150 does not operate by regulating the water supply to Valve 170, but rather by modulating an electric current. Advantageously, in some embodiments, since Controller 150 may modulate the electric signals instead of the water flow to Valve 170, Controller 150 may be installed quickly and effortlessly without disrupting any of the existing pipelines connected to Valve 170. In some embodiments, Controller 150 may be installed as an addition to an existing, conventional sprinkler controller system. In various embodiments, Controller 150 and Valve 170 may be integrated into a single hybrid device or apparatus.

In various embodiments, Router 120 may be configured to communicate with Cloud Platform 110 through Network 130. In various embodiments, Router 120 may be configured to transmit data to Cloud Platform 110. As discussed earlier, in various embodiments, Router 120 may receive Data 160 (e.g., garden parameters) from Sensor 140. In various embodiments, Router 120 may then transmit Data 160 to Cloud Platform 110. In various embodiments, Router 120 may also be configured to receive Data 161 from Cloud Platform 110. As discussed earlier, Router 120 may transmit signals to Controller 150. In particular, Router 120 may transmit signals directing Controller 150 to cause Valve 170 to open and to close. In various embodiments, Router 120 may transmit to Controller 150 signals which it receives from Cloud Platform 110. In various embodiments, Cloud Platform 110 may analyze data, such as Data 160, in order to determine or to generate Data 161. For example, in some embodiments, Cloud Platform 110 may analyze various garden parameters (e.g., soil moisture, soil salinity, soil temperature, soil pH, external temperature, external humidity, light exposure) to determine whether or when to turn on (or off) Valve 170. In various embodiments, Data 161 may include data that is generated by applying one or more statistical analysis techniques to Data 160, including but not limited to extrapolating, interpolating, averaging, or segmenting Data 160. In some embodiments, Cloud Platform 110 may further receive Data 162. In various embodiments, Data 162 may come from any appropriate source or sources, and may include additionally relevant data such as the weather forecast. In some embodiments, Data 162 may include historical data and collective data (e.g., past or present garden parameters from multiple users). In some embodiments, Data 161 may include possible future garden parameters forecast based at least in part on Data 160 and Data 162. In various embodiments, Data 162 may also include user inputs, such as instructions, commands, and any other appropriate types of user feedback. For example, in various embodiments, users may be able to input and transmit to Cloud Platform 110 real life observations (e.g., moistness of the soil, health of plants) and, as will be discussed in more detail below, preferences (e.g., preferred plants, budgets). In various embodiments, Cloud Platform 110 may generate or determine Data 161 based on an analysis of one or both of Data 160 and Data 162.

In addition to Router 120, FIG. 1 further shows that in various embodiments, Cloud Platform 110 may also communicate with Device 181 and Device 182 via Network 130. In various embodiments, Devices 181 and 182 may be any appropriate type of computing and communication device, including but not limited to a smartphone, tablet PC, or personal computer. In various embodiments, Device 181 and Device 182 may each be capable of hosting Application 190. For example, in some embodiments, users may download and install Application 190 onto their respective devices of choice (e.g., Device 181, Device 182). In various embodiments, Application 190 may allow various users to communicate with Cloud Platform 110, including by sending, receiving, and otherwise interacting with various types of data. In particular, in some embodiments, Cloud Platform 110 may be capable of collecting and analyzing data, such as Data 160, from different gardens and over extended periods of time. In addition, in some embodiments, Cloud Platform 110 may keep track of the current status of one or both of Controller 150 and Valve 170. Thus, in various embodiments, users may use Application 190 to interact with (e.g., view) current, historical, and collective sets of data.

In various embodiments, users may also use Application 190 to see the current status of their respective sprinkler systems (e.g., whether Valve 170 is open or closed). In various embodiments, Cloud Platform 110 may transmit one or more alerts, notifications, or recommendations to the user via Application 190. For example, based on Data 160 (e.g., garden parameters measured by Sensor 140) and Data 162 (e.g., historical data and collective data from different users, weather, forecasted garden parameters, user inputs, etc.), Cloud Platform 110 may generate and transmit to the user an alert, notification, or recommendation that instructs the user to perform one or more actions in order to achieve certain garden parameters. In various embodiments, Cloud Platform 110 may recommend actions such as adding additives (e.g., fertilizers to change the pH or salinity in the soil), applying mulch (e.g., to control moisture level and soil temperature), and covering the plants (e.g., to encourage a more humid environment).

In some embodiments, Application 190 may provide one or more options for users to change or to override the current status of their respective sprinkler systems. That is, in some embodiments, a user may request, through Application 190, that Controller 150 force shuts Valve 170. However, as described earlier, it is to be understood that System 100 may, in various embodiments, also operate without Controller 150. In some embodiments, Controller 150 is optional equipment. In those embodiments where Controller 150 is not installed or is not in use, instead of sending commands or instructions to Controller 150 to turn on (and off) Valve 170, Cloud Platform 110 may transmit alerts, notifications, or recommendations to Device 181 or Device 182 instructing the user to manually turn on (and off) Valve 170.

Sprinkler systems are typically installed based on a multi-zone paradigm. That is, a planted area (e.g., garden, lawn, field, golf course) is divided into different zones and each sprinkler valve (or group of sprinkler valves) in the sprinkler system is designated to service a separate zone. Since each sprinkler valve (e.g., Valve 170) may require a separate controller (e.g., Controller 150) in the various embodiments of System 100 described with respect to FIG. 1, System 100 is ideally suited for a planted area with a relatively small number (e.g., two or fewer) zones. However, System 100 may nonetheless be used for a planted area with any number of zones.

Figure 2:
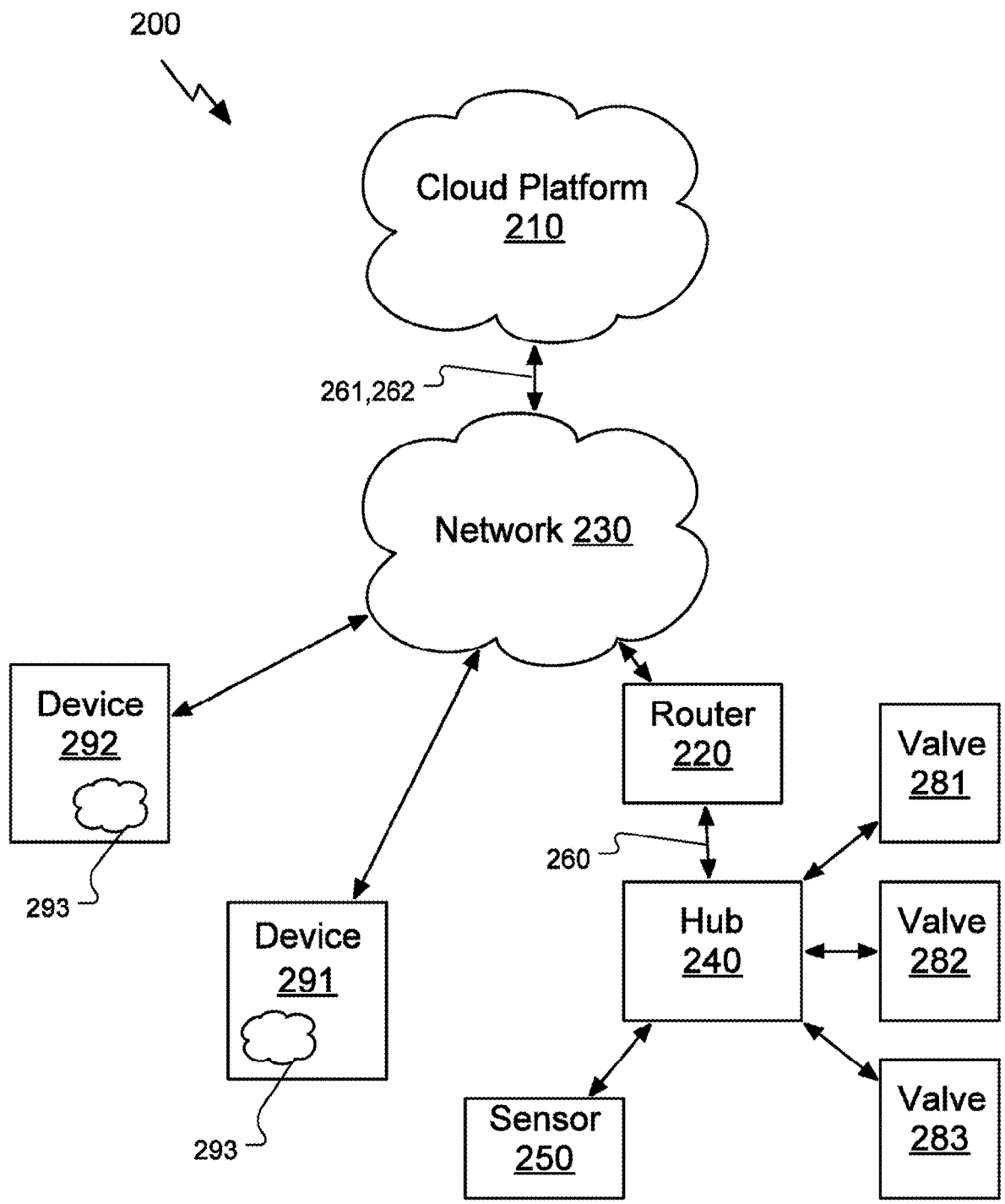
FIG. 2 is a diagram illustrating an embodiment of a system for dynamically collecting, analyzing, and regulating garden parameters.

FIG. 2 is a diagram illustrating an embodiment of a System 200 for dynamically collecting, analyzing, and regulating garden parameters. In various embodiments, System 200 is ideally suited for a planted area with a larger number of zones (e.g., more than two), though it may also be used for a planted area with fewer zones. As shown in FIG. 2, in some of the embodiments described herein, System 200 may comprise a Cloud Platform 210, which may communicate with a wireless Router 220 via Network 230. Meanwhile, according to FIG. 2, in some of the embodiments described herein, Router 220 may further communicate with a Hub 240. In various embodiments, Hub 240 may be Wi-Fi-enabled and may communicate with Router 220 via a Wi-Fi link. In various embodiments, Hub 240 may also communicate with Sensor 250. In various embodiments, Hub 240 and Sensor 250 may be capable of communicating over a low-power, sub-GHz link. In some embodiments, Hub 240 may communicate with Sensor 250 via a 900 MHz long distance radio link. In contrast to System 110, which was described with respect to FIG. 1, in various embodiments of System 200, Sensor 250 may not be required to communicate directly with Router 220 over a Wi-Fi link. Instead, in various embodiments of System 200, Hub 240 may act as a broker or intermediary that centralizes the communication of various types of data between Router 220 and Sensor 250. In the various embodiments of System 200, Sensor 250 may only be required to communicate data over a low-power sub-GHz link. Advantageously, in the various embodiments of System 200, Sensor 250 may be more power efficient than a Wi-Fi enabled counterpart, such as Sensor 140 described with respect to FIG. 1. It is to be understood that, although not shown in FIG. 2, in various other embodiments of System 200, Hub 240 may communicate with any appropriate, necessary, or desired number (e.g., two or more) of sensors (e.g., Sensor 250). It is also to be understood that Hub 240 is optional and in some embodiments of System 200 not shown in FIG. 2, System 200 operates without Controller 150.

In various embodiments, Sensor 250 may communicate with Hub 240 including by transmitting Data 260 to Hub 240. In various embodiments, Data 260 may be generated by Sensor 250 based on or using one or more measurements taken by Sensor 250 (e.g., temperature, humidity, light). In various embodiments, Data 260 may include at least one real time garden parameter, including but not limited to soil moisture, soil salinity, soil temperature, soil pH, external temperature, external humidity, and light exposure. In various embodiments, Sensor 250 may be configured to take measurements according to a predetermined or to a dynamic schedule or frequency, and to transmit Data 260 to Hub 240 in real time or at preset intervals (e.g., hourly, daily, weekly) or at variable intervals, which can change dynamically based on one or more factors such as user input or the frequency of measurements taken by Sensor 140.

In various embodiments, Hub 240 may be used instead of or in place of a conventional sprinkler control system because Hub 240 may be capable of controlling multiple sprinkler valves in a sprinkler system. This is in contrast to the various embodiments of System 100 wherein each valve (e.g., Valve 170) may require a separate controller (e.g., Controller 150). As FIG. 2 illustrates, Hub 240 may control the operations (e.g., opening and closing) of Valves 281, 282, and 283. However, it is to be understood that in various embodiments, Hub 240 may control any appropriate, required, or desired number of valves. In various embodiments, Hub 240 may be capable of opening (or closing) some or all of Valves 281, 282, and 283 including by determining and transmitting one or more control signals to the appropriate valve(s). In various embodiments, Hub 240 may determine which of Valves 281, 282, and 283 to open (or close) and when based at least in part on Data 261 from Router 220. As will be discussed in more detail below, in various embodiments, Data 261 may originate from Cloud Platform 210. In some embodiments, Data 261 may include explicit commands or instructions for Hub 240 to open (or close) some or all of Valves 281, 282, and 283. In some embodiments, Data 261 may include a fully or partially processed data set. Thus, in various embodiments, it is understood that Hub 240 may be capable of executing instructions (or commands) from Cloud Platform 210 to open (or close) some or all of Valves 281, 282, and 283. Instead or in addition, in some embodiments, Hub 240 may be capable of analyzing a fully or partially processed data set from Cloud Platform 210 in order to generate one or more instructions (or commands) to open (or close) some or all of Valves 281, 282, and 283.

Meanwhile, as discussed earlier, in various embodiments, Hub 240 may be capable of communicating with Cloud Platform 210 through wireless Router 220. In various embodiments, Hub 240 may be a Wi-Fi transceiver that transmits to Router 220 various types of data destined for Cloud Platform 210. For example, as discussed earlier, in some embodiments, Hub 240 may receive Data 260 from Sensor 250 over a sub-GHz (e.g., 900 MHz) link. Thus, in some embodiments, Hub 240 may transmit Data 260, whether immediately or according to a preset schedule or frequency, to Cloud Platform 210 through Router 220. In addition, in some embodiments, Hub 240 may be a Wi-Fi transceiver that receives from Router 220 various types of data, including Data 261, from Cloud Platform 210. In various embodiments, Cloud Platform 210, like Cloud Platform 110 discussed with respect to FIG. 1, may analyze data, such as Data 260, in order to determine or to generate Data 261. In various embodiments, Cloud Platform 210 may analyze various garden parameters (e.g., soil moisture, soil salinity, soil temperature, soil pH, external temperature, external humidity, and light exposure) to determine or to generate Data 261. In various embodiments, Data 261 may include data that generated by applying one or more statistical analysis techniques to Data 260, including but not limited to extrapolating, interpolating, averaging, and segmenting Data 260. In some embodiments, Cloud Platform 210 may further receive Data 262. In various embodiments, Data 262 may come from any appropriate source or sources, and can include additionally relevant data such as the weather forecast. In some embodiments, Data 262 may include historical data and collective data (e.g., past or present garden parameters from multiple users or gardens). As will be discussed in more detail below, Data 262 may also include user inputs, such as instructions, commands, and any type of appropriate user feedback. For example, in various embodiments, users may be able to input and transmit to Cloud Platform 210 real life observations (e.g., moistness of the soil, health of plants) and, as will be discussed in more detail below, preferences (e.g., preferred plants, budgets). In various embodiments, Cloud Platform 210 may generate or determine Data 261 based on an analysis of one or both of Data 260 and Data 262. In some embodiments, Data 261 may include possible future garden parameters forecasted based at least in part on Data 260 and Data 262. In some embodiments, Cloud Platform 210 may analyze one or both of Data 260 and Data 262 to determine whether and when to turn on (or off) some or all of Valves 281, 282, and 283. Thus, in some embodiments, Data 261 may include commands or instructions for Hub 240 to turn on (or off) some or all of Valves 281, 282, and 283. Alternately or in addition, in some embodiments, Cloud Platform 210 may fully or partially analyze one or both of Data 260 and Data 262 and then generate a refined, condensed, edited, or otherwise processed data set based on one or both of Data 260 and Data 261. As such, in some embodiments, Data 261 may include a fully or partially processed data set in addition to or in lieu of instructions (or commands) directed toward some or all of Valves 281, 282, and 283.

In addition to Router 220, FIG. 2 further shows that in various embodiments, Cloud Platform 210 may also communicate with Device 291 and Device 292 via Network 230. In various embodiments, Devices 291 and 292 may be any appropriate type of computing and communication device, including but not limited to a smartphone, tablet PC, or personal computer. In various embodiments, Device 291 and Device 292 may each be capable of hosting Application 293. For example, in some embodiments, users may download and install Application 293 onto their respective devices of choice (e.g., Device 291, Device 292). In various embodiments, Application 293 may allow various users to communicate with Cloud Platform 210, including by sending, receiving, and otherwise interacting with various types of data. In particular, in some embodiments, Cloud Platform 210 may be capable of collecting and analyzing data, such as Data 260, from different gardens and over extended periods of time. In addition, in some embodiments, Cloud Platform 210 may keep track, either directly or via Hub 240, of the current status of Valves 281, 282, and 283. Thus, in various embodiments, users may use Application 293 to interact with (e.g., view) current, historical, and collective sets of data.

In various embodiments, users may also use Application 293 to receive updates on the current status of their respective sprinkler systems (e.g., whether some or all of Valves 281, 282, and 283 are open or closed). In various embodiments, Cloud Platform 210 may also transmit one or more alerts, notifications, or recommendations to the user via Application 293. For example, based on Data 260 (e.g., garden parameters measured by Sensor 140) and Data 262 (e.g., historical data and collective data from different users, forecasted garden parameters, and user inputs), Cloud Platform 210 may generate and transmit to the user an alert, notification, or recommendation that instructs the user to perform one or more actions in order to achieve certain garden parameters. In various embodiments, Cloud Platform 210 may recommend actions such as adding additives (e.g., fertilizers to change the pH or salinity in the soil), applying mulch (e.g., to control moisture level and soil temperature), and covering the plants (e.g., to encourage a more humid environment).

In some embodiments, Application 293 may provide one or more options for users to change or to override the current status of their respective sprinkler systems. That is, in some embodiments, a user may request, through Application 293, that Hub 240 force shuts some or all of Valves 281, 282, and 283. However, as discussed earlier, it is to be understood that System 240 may, in various embodiments, also operate without Hub 240. In some embodiments, Hub 240 is optional equipment. In those embodiments where Hub 240 is not installed or is not in use, instead of sending commands or instructions to Hub 240 to turn on (and off) some or all of Valves 281, 282, and 283, Cloud Platform 210 may transmit alerts, notifications, or recommendations to Device 281 instructing the user to manually turn on (and off) some or all of Valves 281, 282, and 283.

As discussed earlier, in some embodiments of System 100 described with respect to FIG. 1, at least one sensor (e.g., Sensor 140) and one controller (e.g., Controller 150) may communicate directly with Router 120 via a wireless link (e.g., Wi-Fi). In some embodiments, it is to be understood that System 100 may include any appropriate, required, or desired number of sensors, controllers, and sensor-controller hybrids. As discussed earlier with respect to FIG. 2, in some embodiments of System 200, at least one sensor (e.g., Sensor 250), may communicate directly with a hub (e.g., Hub 240) over a wireless link (e.g., low power, sub-GHz link). As with System 100, in various embodiments of System 200, any appropriate, required, or desired number of sensors may be used. However, particularly in larger gardens, one or more devices may be out of range. For example, in some embodiments of System 100, one or more sensors, controllers, and sensor-controller hybrids may be unable to directly communicate with the router as a result of distance. Likewise, in some embodiments of System 200, one or more sensors may be outside of the hub's range. Under those circumstances, in some embodiments, two or more devices may form an ad-hoc or decentralized network. In some embodiments, data may be communicated amongst a group, sequence, or collection of devices until it reaches a device that is within range. For example, in some embodiments of System 100, one sensor, controller, or sensor-controller hybrid may communicate with one or more other sensors, controllers, or sensor-controllers over a wireless link (e.g., Wi-Fi, sub-GHz, ZigBee, Bluetooth) rather than directly with the router. In some embodiment of System 100, data may be passed along various sensors, controllers, or sensor-controller hybrids until it is within the range of the router. In a similar fashion, in some embodiments of System 200, one sensor may communicate with one or more other sensors over a wireless link (e.g., Wi-Fi, sub-GHz, ZigBee, Bluetooth) instead of with the hub, forming an ad-hoc or decentralized network such that data is forwarded from one sensor to another sensor until it is within the range of the hub. In some embodiments of System 100 or 200, an ad-hoc or decentralized network may be used as described above for other reasons, such as to minimize power consumption in transmitting data.

Figure 3:
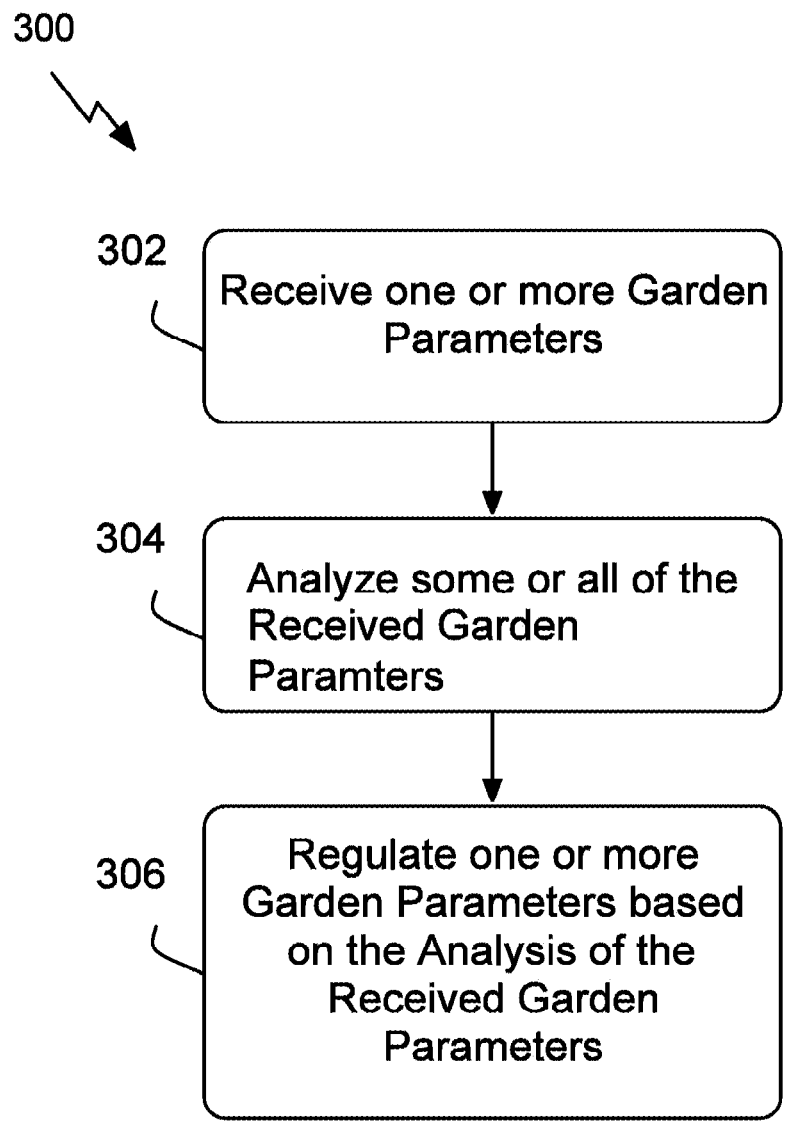
FIG. 3 is a flowchart illustrating an embodiment of a process for dynamically collecting, analyzing, and regulating garden parameters.

FIG. 3 is a flowchart illustrating an embodiment of a Process 300 for dynamically collecting, analyzing, and regulating garden parameters. In various embodiments, Process 300 may be performed by or at a cloud platform such as Cloud Platform 110 or Cloud Platform 210.

At 302, one or more garden parameters may be received. In various embodiments, the garden parameters received at the cloud platform may originate from one or more sensors (e.g., Sensor 140, Sensor 250) or sensor-controller hybrids. As discussed earlier, sensors (e.g., Sensor 140 and Sensor 250) as well as sensor-controller hybrids may be capable of measuring various garden parameters. In various embodiments, the garden parameters received at the cloud platform may originate from sensors that are installed in one or more different gardens. In various embodiments, garden parameters may include but are not limited to soil moisture, soil salinity, soil temperature, soil pH, external temperature, external humidity, and light exposure.

At 304, some or all of the garden parameters received at 302 may be analyzed. In various embodiments, one or more statistical analysis techniques may be applied. At 306, one or more garden parameters may be regulated based at least in part on the analysis of the received garden parameters. In various embodiments, regulating garden parameters may include changing or adjusting one or more current garden parameters in a garden. For example, in some embodiments, the cloud platform may analyze data including garden parameters from one or more gardens, the weather forecast, and user inputs to determine whether or not to turn on (or off) one or more sprinkler valves, and for how long. In some embodiments, turning on (or off) sprinkler valves for a certain period of time may cause desired or necessary changes in one or more garden parameters. For example, if one or more garden parameters (e.g., soil moisture, external humidity) indicate that the conditions in a garden are too arid, then the cloud platform may turn on one or more sprinkler valves for a certain amount of time in order to alleviate the aridity. Alternately or in addition, in some embodiments, the cloud platform may analyze data including garden parameters from one or more gardens, weather forecast, and user inputs to determine that the garden requires changes that entail human intervention, such as the addition of additives (e.g., fertilizer) and the application of mulch and other coverings. In some embodiments, the cloud platform may be configured to transmit an alert, notification, or recommendation to the user to perform the necessary actions.

Calibration and Optimization

As discussed with respect to FIG. 1 and FIG. 2, in various embodiments, the systems and methods described herein may utilize one or more sensors (e.g., Sensor 140, Sensor 250) or sensor-controller hybrids that are capable of measuring a variety of garden parameters. Examples of garden parameters include but are not limited to soil moisture, soil salinity, soil temperature, soil pH, external temperature, external humidity, and light exposure. In various embodiments, a sensor (or sensor-controller hybrid) may be configured to take measurements according to a predetermined or to a dynamically generated schedule or frequency. For example, in some embodiments, the sensor may be configured to take measurements at preset intervals (e.g., hourly, daily, weekly). In some embodiments, the sensor may be configured to take measurements at dynamically determined intervals. In particular, in some embodiments, the sensor may be configured to take measurements according to a dynamically generated schedule or frequency that is optimized based on specific garden conditions. For example, conditions in some gardens are volatile and change frequently while the conditions in other gardens remain relatively stable over time. Moreover, it is also often the case that some garden parameters fluctuate more frequently than others. Therefore, in some embodiments, the sensor may be configured to take the minimum number of measurements necessary to capture and provide an accurate and comprehensive range of data.

In some embodiments, a cloud platform (e.g., Cloud Platform 110, Cloud Platform 220) may receive data from the sensor that includes the various measurements taken by the sensor. In some embodiments, based on characteristics or patterns associated with the data, particularly over time, the cloud platform may be able to determine when or how frequently the sensor should optimally take its measurements. In some embodiments, data patterns or characteristics may include volatility and fluctuations that are best observed from a data set that is collected over a more extended period of time. In some embodiments, the cloud platform may develop a data profile that is specific to each garden. In some embodiments, the data profile for a garden may be built using data that includes past or historical garden parameters (i.e., different garden parameters that are collected over a period of time). Thus, in various embodiments, the cloud platform may be able to detect patterns or characteristics that indicate various levels of fluctuation or volatility based on the data profile for each garden. Thus, in some embodiments, based on data characteristic or patterns, the cloud platform may send commands or instructions to the sensor to take one or more measurements. In some embodiments, based on data characteristics or patterns, particularly with respect to individual garden parameters, the cloud platform may instruct or command the sensor to measure different garden parameters according to different schedules or frequencies. In various embodiments, the schedule or the frequency for the sensor to take measurements may be updated, adjusted, or refined as more data is collected over time and added to a garden's data profile.

As discussed earlier, sprinkler systems are typically set up into different zones. As such, in various embodiments, the sprinkler valve(s) (e.g., Valve 170, Valves 281-283) in each zone may be controlled separately based at least in part on the varying conditions in each zone. In various embodiments, regardless of the size of the garden and the number of zones, any appropriate, required, or desired number of sensors or sensor-controller hybrids may be deployed. For example, one user may install one sensor in each zone or multiple sensors in each zone. In particular, in some embodiments, one sensor can be shared across multiple zones (i.e., used in two or more zones). Advantageously, the portability and mobility of sensors and sensor-hybrids across different zones allow the various embodiments of the systems and the methods described herein to be implemented with a minimal amount of equipment, cost, and effort. Suppose, for example, that Alice wants to purchase and use only one sensor to measure garden parameters in two zones (e.g., Zone A, Zone B) in her backyard. In various embodiments, Alice may install an application (e.g., Application 190, Application 293) onto her smartphone or any other type of computing and communication device (e.g., personal computer, tablet PC). In various embodiments, using the application, Alice may input or otherwise indicate to the cloud platform the current zone that the sensor is in. Furthermore, in various embodiments, Alice may use the application to input or otherwise indicate to the cloud platform whenever the sensor is moved from one zone to another (e.g., from Zone A to Zone B, and vice versa). In those embodiments where a single sensor is used across multiple zones, the cloud platform may attribute garden parameters to the correct zone based on inputs or indications from the user. To continue the example, based on Alice's input or indication that the sensor is in Zone A, the cloud platform may attribute garden parameters received from the sensor to Zone A and not Zone B.

User Interactivity—Plant Recommendation

As discussed earlier, in various embodiments, users may communicate with the cloud platform (e.g., Cloud Platform 110, Cloud Platform 210) via the application (e.g., Application 190, Application 293), including by sending, receiving, and otherwise interacting with various types of data. Also as discussed earlier, in various embodiments, the cloud platform (e.g., Cloud Platform 110, Cloud Platform 210) may receive and analyze a variety of different types of data, including but not limited to data from sensors or sensor-controller hybrids (e.g., garden parameters from different users and gardens), weather forecast, user inputs, etc. In addition, the cloud platform may store at least a portion of the data to develop current and historical data profiles for a variety of different entities or groups of entities, including but not limited to different users, gardens, neighborhoods, regions, etc. In fact, in various embodiments, the cloud platform may be able to analyze, process, and store data in any appropriate manner, including but not limited to applying statistical analysis techniques such as aggregating, segmenting, averaging, interpolating, and extrapolating the data.

In various embodiments, the cloud platform may be able to recommend plant selections for a user. In some embodiments, the cloud platform may deliver its recommendations to the user via the application. In some embodiments, the cloud platform may determine an appropriate plant selection based on garden parameters from one or more sensors in the user's garden. For example, the appropriate plant selection may be determined based on current, historical, or predicted garden parameters from the user's own garden. Alternately or in addition, in some embodiments, the appropriate plant selection may be determined based on the type(s) of plants that have been successfully grown in a reference area, which includes but is not limited to identical, similar, or adjacent area(s). In various embodiments, based on criteria that include but are not limited to the availability or volume of data, the cloud platform may further determine an appropriately sized or situated reference area in order to determine an appropriate plant selection for a user's garden.

In some embodiments, in addition to garden parameters, the cloud platform may determine an appropriate plant selection further based on user preferences. In various embodiments, the user may stipulate his or her preferences at any level of specificity and based on any appropriate type of parameters (e.g., plant characteristics such as color, size, required maintenance). For example, Alice may indicate to the cloud platform (via the installed application) that she likes or prefers a specific type or species of peony (e.g., Chinese or Japanese peony). Alternately, Alice may indicate to the cloud platform that she likes or prefers plants that bear pink colored flowers. Based on the stated preference, the cloud platform may, in some embodiments, recommend plants that are appropriate for the user's garden. However, it can often be the case that a user indicates a preference for a plant or type of plant that is not appropriate given the user's garden parameters. Thus, in some embodiments, the cloud platform may recommend plant alternatives that are more ideal or better suited for the user's garden (i.e., plants that can survive or thrive based on the garden parameters from the user's garden) and which are similar to the preferred plant or type of plant. In some embodiments, the cloud platform's suggestions or recommendations may be displayed, via the application, in order of each plant's level of similarity to the preferred plant or type of plant. In some embodiments, the cloud platform's plant suggestions or recommendations may be displayed, in addition or instead, in order of the likelihood for each of the suggested plants to survive in the user's garden. In some embodiments, the cloud platform's plant suggestions or recommendations may be displayed with an option (e.g., a hyperlink) for the user to be directed to one or more e-commerce websites (e.g., Amazon.com®, Lowe's®, Home Depot®) that sells, carries, or can otherwise provide the plant(s).

In some embodiments, in addition to or instead of displaying plant suggestions or recommendations, the user may be given an option to enroll (via the application) in a plant subscription program (e.g., seed or plant of the month). In some embodiments, enrollment in the plant subscription program entitles the user to a regularly scheduled (e.g., monthly, quarterly) delivery of plants or seeds that may be curated from the cloud platform's plant suggestions or recommendations. In some embodiments, the cloud platform may determine and deliver (via the application) advertisements and links to other services (proprietary or third-party) that are appropriate for the user based on the user's garden parameters (e.g., soil quality) and inputs (e.g., preferred plants).

In some embodiments, the cloud platform may determine an appropriate plant selection based on the user's budget. In various embodiments, the cloud platform may take into consideration the user's budget in addition to or instead of the user's stated preferences. In various embodiments, the user's budget may include a one-time, initial setup cost. That is, the user may specify how much he or she can or would like to spend on plants and seeds for a garden. In various embodiments, the user's budget may further include a maintenance cost. For example, the user may specify, in addition to or instead, how much he or she can or would like to spend on maintaining the plants in the garden (e.g., water, fertilizer, mulch, etc.).

As discussed earlier, the cloud platform may use a variety of data (e.g., garden parameters, weather forecast, user inputs, etc.) to determine and to generate data indicating when the sprinkler system in a user's garden should be open (and closed). In some embodiments, the cloud platform may send commands or instructions to automatically turn on (and off) some or all of the valves in the sprinkler system. In some embodiments, the cloud platform may send instructions to the user to manually turn on (and off) some or all of the valves in the sprinkler system. In various embodiments, the cloud platform may collect and analyze a variety of data, including but not limited to current (e.g., the latest set of garden parameters), historical (e.g., garden parameters measured over a certain period time), and forecasted data (e.g., the weather forecast, extrapolated garden parameters). In various embodiments, the cloud platform may collect and analyze data from a variety of sources, including but not limited to data collected by sensors in the user's garden (e.g., Sensor 140, Sensor 250), data collected by sensors in other users' gardens, the weather forecast, and user feedback (e.g., real life observations of garden parameters and plant conditions). Thus, in various embodiments, the cloud platform may be capable of dynamically determining and regulating the conditions in a user's garden based on current, historical, and forecasted data. In various embodiments, a user may use the application to instruct the cloud platform to emulate or recreate the garden parameters in another user's garden. In an earlier example, Alice was unable to grow the same kind of peony that thrives in her neighbor Bob's yard. Suppose both Alice and Bob have installed System 100, as described with respect to FIG. 1, or System 200, as described with respect to FIG. 2. In this case, the cloud platform would have access to garden parameters from both Alice and Bob's gardens. The garden parameters from Bob's garden have proven to be conducive to cultivating peonies. As such, in some embodiments, Alice can instruct the cloud platform to regulate or modify her garden parameters, including by turning on and off one or more sprinkler valves and recommending one or more actions on the part of Alice (e.g., fertilizer, mulch, coverings), so that the garden parameters in Alice's garden match the garden parameters in Bob's garden.

In various embodiments, the cloud platform (e.g., Cloud Platform 110, Cloud Platform 210) may be configured to continuously interact with a user, a garden, and a microclimate (i.e., the regional environment and characteristics of the user's garden). In various embodiments, a control system may be paradigmatic of the interactions and the nexus between the cloud platform, the user, the garden, and the microclimate.

Figure 4A:
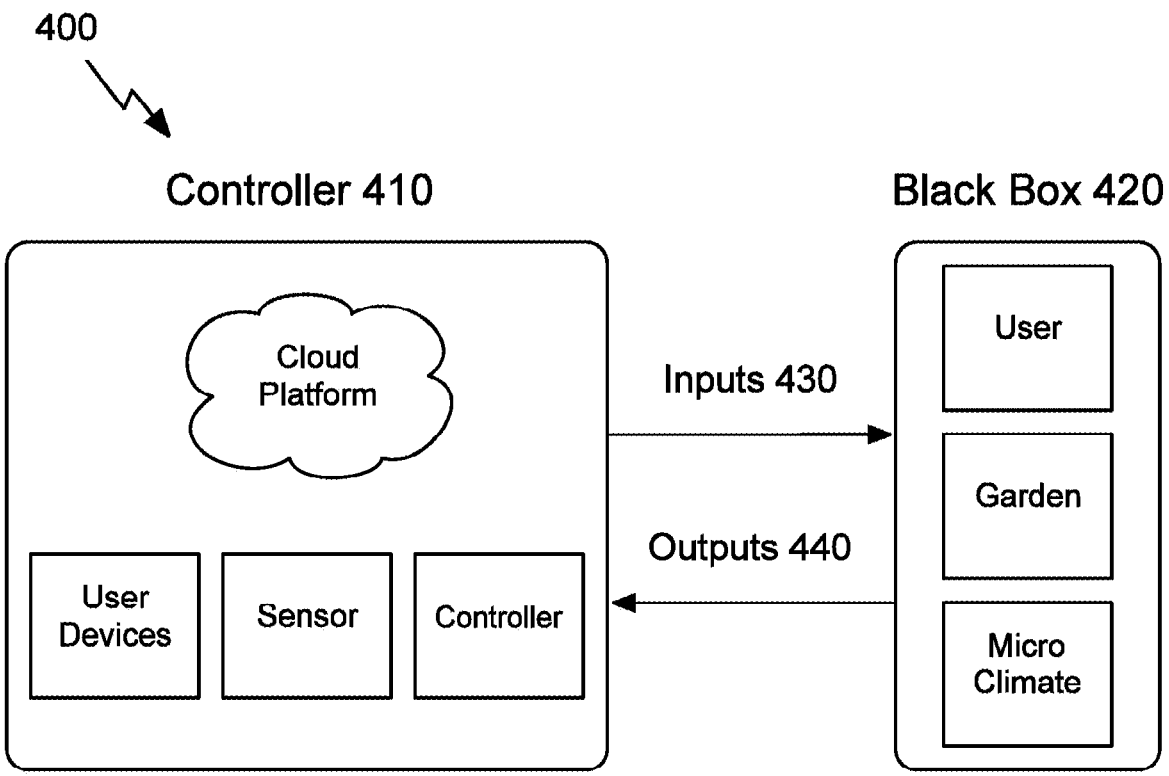
FIG. 4A is a diagram illustrating an embodiment of a control system.

FIG. 4A is a diagram illustrating a Control System 400. As shown in FIG. 4A, in various embodiments, Control System 400 may comprise a Controller 410 and a Black Box 420. In various embodiments, Controller 410 may correspond to the system for dynamically collecting, analyzing, and regulating garden parameters (e.g., System 100, System 200) described herein. As described with respect to FIG. 1 and FIG. 2, various embodiments of the system for dynamically collecting, analyzing, and regulating garden parameters may include some combination of the following components: a cloud platform (e.g., Cloud Platform 110, Cloud Platform 220), sensors (e.g., Sensor 140, Sensor 250), user devices (e.g., Devices 181-182, Devices 291-292), and a hub (e.g., Hub 240) or valve controllers (e.g., Controller 150). Meanwhile, in various embodiments, Black Box 420 represents a typical garden ecosystem containing a user (e.g., Alice), a garden (e.g., Alice's garden), and a microclimate (e.g., Mission Valley in San Diego, CA). In various embodiments, Controller 410 may be configured to determine inputs (e.g., Inputs 430) into Black Box 420 based on the outputs (e.g., Outputs 440) from Black Box 420. In various embodiments, Inputs 430 from Controller 410 may include a variety of data that can be used to alter and is otherwise capable of altering conditions inside Black Box 420. In various embodiments, Outputs 440 may include a variety of data that is indicative of the conditions inside Black Box 420, including but not limited to readings, measurements, and feedback from the different constituents of Black Box 420 (e.g., the user, garden, and microclimate). In various embodiments, Controller 410 may continuously refine Inputs 430 based on Outputs 440 in order to determine a set of inputs that yields one or more ideal, desired, expected, or required outputs. In various embodiments, Controller 410 may determine a set of inputs that yields the ideal, desired, expected, or required outputs by satisfying requirements or conditions imposed by some or all of the constituents of Black Box 420. In various embodiments, Controller 410 may determine a set of inputs that would improve, influence, and otherwise change the current conditions in Black Box 420 (as indicated by a previous set of outputs) so that the next set of outputs from Black Box 420 would approximate or match the ideal, desired, expected, or required outputs.

For example, in some embodiments, users may have certain characteristics, which are typically manifest as one or more preferences for certain plants or for a particular budget. Meanwhile, in various embodiments, the user's garden may also exhibit a number of characteristics. Characteristics of the garden may be, in some embodiments, captured in the garden parameters measured by various sensors or in the user's observations. Finally, in some embodiments, the microclimate may host a variety of characteristics as well, including weather conditions such as sun, snow, rain, high winds, etc. Thus, in various embodiments, Outputs 440 may include readings and measurements of some or all of the characteristics of the constituents of Black Box 420. For example, in some embodiments, Outputs 440 may include but are not limited to user input, weather (e.g., current and forecasted), and various measured garden parameters. Based on Outputs 440, in various embodiments, Controller 410 may determine Inputs 430, which may include, as examples, commands and instructions to open (and close) sprinkler valves, and alerts, notifications, and recommendations to the user to perform one or more actions (e.g., water, fertilize, apply mulch, cover plant, etc.). As shown in FIG. 4A, in the various embodiments Control System 400, Controller 410, and Black Box 420 may be part of an iterative feedback loop. In various embodiments, Inputs 430 may both regulate and continuously evolve based on Outputs 440. In various embodiments, Outputs 440 may both change as a result of Inputs 430 and perpetuate the evolution of Inputs 430.

Figure 4B:
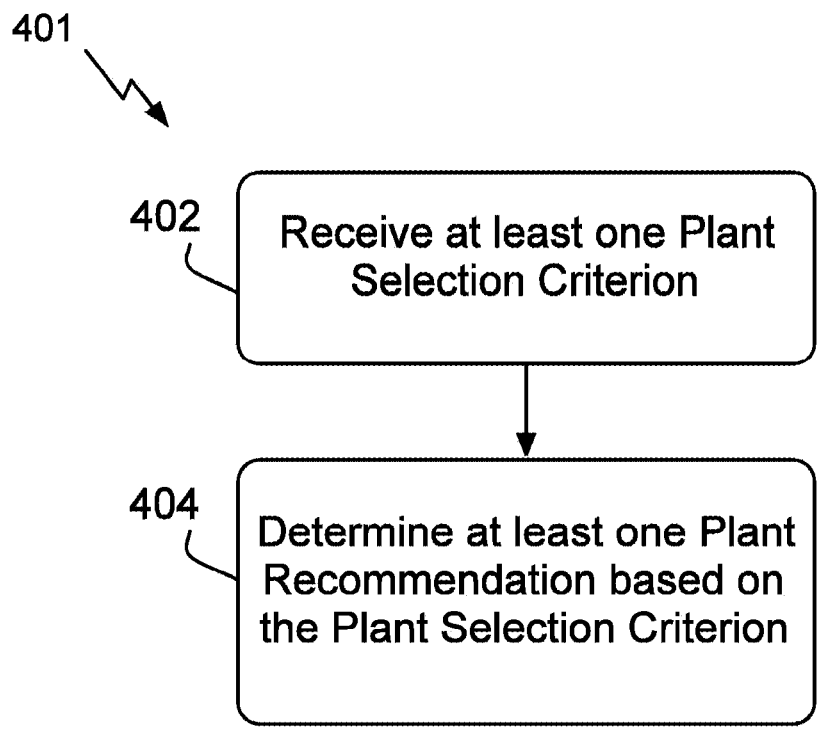
FIG. 4B is a flowchart illustrating an embodiment of a process for making plant recommendations.

FIG. 4B is a flowchart illustrating an embodiment of a Process 401 for making plant recommendations. In various embodiments, Process 401 may be performed by or at a cloud platform (e.g., Cloud Platform 110, Cloud Platform 210). At 402, at least one plant selection criterion may be received. In various embodiments, plant selection criteria may originate from a number of different sources, including but not limited to sensors installed in the user's garden, and plant or budget preferences specified by the user.

At 404, at least one plant to recommend may be determined based at least in part on the selection criteria. For example, in some embodiments, the cloud platform may determine one or more plants to recommend based on the current, historical, or forecasted garden parameters in the user's garden. Alternately or in addition, in some embodiments, the cloud platform may determine one or more plants to recommend based on preferences stated by the user, including but not limited to the user's budget and the user's preferred plant selections. Furthermore, in some embodiments, in scenarios where the user's preferred plant selections are inappropriate or unsuited for the user's garden (e.g., based on the user's current, historical, or forecasted garden parameters), the cloud platform may be able to recommend plants that are similar to the user's preferred plants but can also tolerate or thrive in the user's garden.

User Interface

In the various embodiments of the systems and methods described herein, various garden events may be converted into one or more appropriate units of accounting. In various embodiments, examples of garden events may include but are not limited to turning on the sprinkler system, rainfall, fertilizing, and applying mulch and other coverings. In particular, in some embodiments, garden events may be converted into an appropriate currency (e.g., USD, Euros) in order to reflect the expenditures and savings generated by each garden event. As one example, in various embodiments, the cloud platform (e.g., Cloud Platform 110, Cloud Platform 210) may keep track of the current status of sprinkler valves (e.g., Valve 170, Valves 281-283). Thus, in various embodiments, the cloud platform may determine when each sprinkler system was turned on and for how long. Consequently, in various embodiments, the cloud platform may estimate the amount of water that was used and convert this information into a dollar amount (e.g., it costs $5 to water Zone A for 30 minutes).

In another example, the cloud platform may be configured to send an alert, notification, or recommendation that instructs a user to perform one or more actions. In some embodiments, the alert, notification, or recommendation may further include an estimated cost associated with the instructed actions. For instance, the cloud platform may determine based on a variety of data including a difference between the current pH or salinity level of the soil, and the ideal, desired, required, or expected level(s), that a certain amount of fertilizer is needed. In some embodiments, the cloud platform's alert, notification, or recommendation instructing the user to apply fertilizer to the user's garden may include the cost for the amount of fertilizer needed.

In various embodiments, the cloud platform may also estimate the amount of savings generated by a garden event. For example, if it rained profusely one day, based on data such as the weather forecast and the level of moisture in the soil after the rain, the cloud platform may determine and indicate to the user that his or her garden will not have to be watered for at least 8 days, generating a savings of $20. In various embodiments, the cloud platform may further estimate the cost of recreating ideal garden parameters or the specific garden parameters found in another garden. In an earlier example, Alice wishes to recreate the garden parameters in Bob's garden. The cloud platform may, in various embodiments, approximate the overall or individual cost corresponding to the amount of water, fertilizer, and mulch that are required to transform the existing conditions in Alice's garden so that the two gardens would exhibit identical or near-identical garden parameters.

In various embodiments, the cloud platform may analyze various types of data and generate different metrics indicating the efficiency of a user's sprinkler system. As discussed earlier, in various embodiments, the cloud platform may be able to estimate the amount of water usage based on information regarding when the user's sprinkler system was in use. In various embodiments, the cloud platform may assess the amount of water usage relative to one or more different benchmarks, including but not limited to an ideal, desired, required, and expected set of garden parameters. Suppose, for example, that Alice's sprinkler system was turned on for a certain period time (e.g., X minutes). In some embodiments, the cloud platform may estimate what the expected level of moisture in Alice's garden should be after X minutes of watering. In some embodiments, the cloud platform's estimate may be generated based on a host of different types of data (e.g., Data 161-162, Data 261-262), including but not limited to current weather conditions (e.g., temperature, humidity, wind), historical garden parameters measurements from both Alice and other similar gardens taken before and after watering, and empirical statistics. In various embodiments, the cloud platform may determine the efficiency of Alice's sprinkler system as a measure of how close (e.g., expressed as a percentage) the moisture level in Alice's garden is to the expected moisture level. Alternately, returning again to the previous example where Alice is attempting to recreate the garden parameters in Bob's garden, in some embodiments, the cloud platform may also determine the efficiency of Alice's sprinkler system in terms of the proximity between the moisture level in her garden after X minutes of watering and the ideal moisture level found in Bob's garden.

In various embodiments, the cloud platform may also take into account the cost of utilities, such as via electric or water rates, to determine when it is most cost-efficient to operate a sprinkler system. In some embodiments, a user may be able to select a cost-efficient profile, which may cause the cloud platform to adjust how it regulates the one or more garden parameters or determines plant recommendations based on the cost of utilities. In various embodiments, the cloud platform may estimate the amount of resources from a utility that would be used for an event and convert this information into a dollar amount (e.g., it costs $5 to water Zone A for 30 minutes at 6 AM, it costs $10 to water Zone A for 30 minutes at 2 PM). In various embodiments, the cloud platform may also take into account legal restrictions, such as water restrictions, to determine when operating a sprinkler system is permissible. In such embodiments, the cloud platform may regulate the one or more garden parameters to avoid operating a sprinkler system during impermissible times or notify a user that a legal restriction may apply to their garden for a watering time selected by a user.

Figure 5:
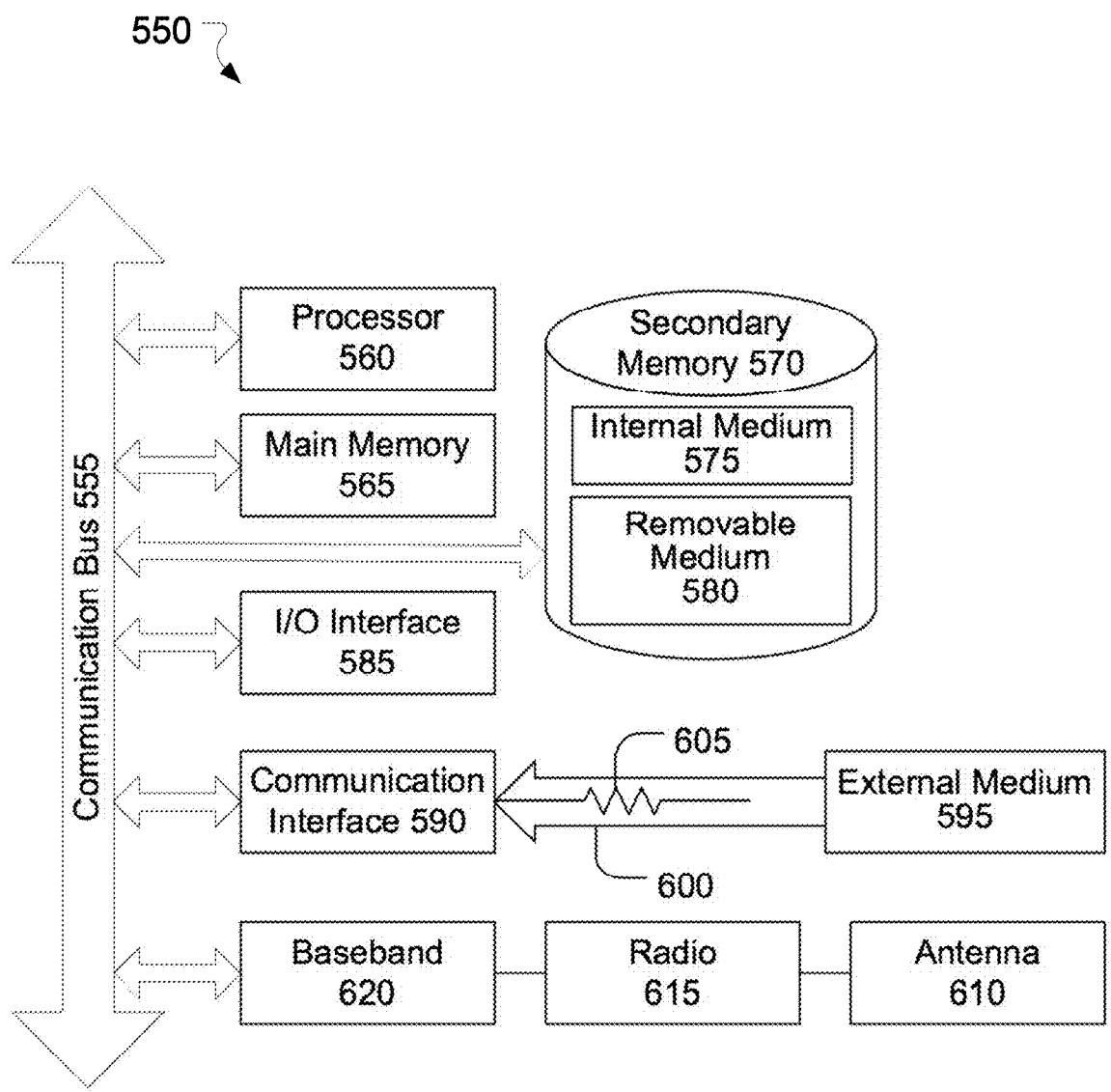
FIG. 5 illustrates an example of a computing environment including a computing device suitable for use in some embodiments.

FIG. 5 is a block diagram illustrating an embodiment of a wired or wireless System 550 that may be used in connection with the various embodiments described herein. For example, System 550 may be used to implement Devices 181-182 as described with respect to FIG. 1, as well as Devices 291-292 and Hub 240, as described with respect to FIG. 2. In some embodiments, System 550 may be a conventional personal computer, computer server, personal digital assistant, smart phone, tablet computer, or any other processor-enabled device that is capable of wired or wireless data communication. However, it is to be understood that other computer systems or architectures may be also used, as will be clear to those skilled in the art.

System 550 may include one or more processors, such as Processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., a digital signal processor), a slave processor subordinate to the main processing system (e.g., a back-end processor), an additional microprocessor or controller for dual or multiple processor systems, or a coprocessor. Such auxiliary processors may be discrete processors or may be integrated with Processor 560.

Processor 560 may be connected to a Communication Bus 555. Communication Bus 555 may include a data channel for facilitating information transfer between storage and other peripheral components of System 550. Communication Bus 555 may further provide a set of signals used for communication with Processor 560, including a data bus, address bus, and control bus (not shown). Communication Bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPM"), IEEE 696/S-100, etc.

System 550 may include a Main Memory 565 and may also include a Secondary Memory 570. Main Memory 565 provides storage of instructions and data for programs executing on Processor 560. Main Memory 565 is typically semiconductor-based memory such as dynamic random access memory ("DRAM") or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), etc., including read only memory ("ROM").

Secondary Memory 570 may optionally include an internal memory (Internal Medium 575) or a Removable Medium 580, for example a floppy disk drive, a magnetic tape drive, a compact disc ("CD") drive, a digital versatile disc ("DVD") drive, etc. Removable Medium 580 is read from or written to in a well-known manner. Removable Medium 580 may be, for example, a floppy disk, magnetic tape, CD, DVD, SD card, etc.

Removable Medium 580 is a non-transitory computer readable medium having stored thereon computer executable code (i.e., software) or data. The computer software or data stored on Removable Medium 580 is read into System 550 for execution by Processor 560.

In alternative embodiments, Secondary Memory 570 may include other similar methods of allowing computer programs or other data or instructions to be loaded into System 550. Such methods may include, for example, an external storage medium (External Medium 595) and a Communication Interface 570. Examples of External Medium 595 may include an external hard disk drive or an external optical drive, or an external magneto-optical drive.

Other examples of Secondary Memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media (Removable Medium 580) and Communication Interface 590, which allow software and data to be transferred from External Medium 595 to System 550.

System 550 may also include an input/output ("I/O") interface, I/O Interface 585. I/O Interface 585 facilitates input from and output to external devices. For example I/O Interface 585 may receive input from a keyboard or mouse and may provide output to a display. I/O Interface 585 is capable of facilitating input from and output to various alternative types of human interface and machine interface devices.

System 550 may also include a Communication Interface 590. Communication Interface 590 allows software and data to be transferred between System 550 and external devices (e.g. printers), networks, or information sources. For example, computer software or executable code may be transferred to System 550 from a network server via Communication Interface 590. Examples of Communication Interface 590 include a modem, a network interface card ("NIC"), a wireless data card, a communications port, a PCMCIA slot and card, an infrared interface, and an IEEE 1394 fire-wire.

Communication Interface 590 may implement industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via Communication Interface 590 are generally in the form of electrical communication signals 605. These signals 605 are provided to Communication Interface 590 via a communication channel 600. In one embodiment, the communication channel 600 may be a wired or wireless network, or any variety of other communication links. Communication channel 600 carries signals 605 and may be implemented using a variety of wired or wireless communication means including wire or cable, fiber optics, conventional phone line, cellular phone link, wireless data communication link, radio frequency ("RF") link, or infrared link.

Computer executable code (i.e., computer programs or software) may be stored in Main Memory 565 or Secondary Memory 570. Computer programs may also be received via Communication Interface 590 and stored in Main Memory 565 or Secondary Memory 570. Such computer programs, when executed, enable System 550 to perform the various functions as previously described.

In this description, the term "computer readable medium" is used to refer to any non-transitory computer readable storage media used to provide computer executable code (e.g., software and computer programs) to System 550. Examples of these media include Main Memory 565, Secondary Memory 570 (including Internal Medium 575, Removable Medium 580, and External Medium 595), and any peripheral device communicatively coupled with Communication Interface 590 (including a network information server or other network device). These non-transitory computer readable mediums are used to provide executable code, programming instructions, and software to System 550.

In an embodiment that is implemented using software, the software may be stored on a computer readable medium and loaded into System 550 by way of Removable Medium 580, I/O Interface 585, or Communication Interface 590. In such an embodiment, the software is loaded into System 550 in the form of electrical communication signals 605. The software, when executed by Processor 560, causes Processor 560 to perform the inventive features and functions previously described herein.

System 550 may also include optional wireless communication components that may facilitate wireless communication over a voice or data network. The wireless communication components may comprise an antenna system (Antenna 610), a radio system (Radio 615) and a baseband system (Baseband 620). In System 550, radio frequency ("RF") signals may be transmitted or received over the air by Antenna 610 under the management of Radio 615.

In one embodiment, Antenna 610 may comprise one or more antennae and one or more multiplexors (not shown) that perform a switching function to provide Antenna 610 with transmit and receive signal paths. In the receive path, received RF signals may be coupled from a multiplexor to a low noise amplifier (not shown) that amplifies the received RF signal and sends the amplified signal to Radio 615.

In alternative embodiments, Radio 615 may comprise one or more radios that are configured to communicate over various frequencies. In one embodiment, Radio 615 may combine a demodulator (not shown) and modulator (not shown) in a single integrated circuit ("IC"). The demodulator and modulator may also alternatively be separate components. In the incoming path, the demodulator strips away the RF carrier signal leaving a baseband receive audio signal, which is sent from Radio 615 to Baseband 620.

If the received signal contains audio information, Baseband 620 decodes the signal and converts it to an analog signal. Then the signal is amplified and sent to a speaker. Baseband 620 also receives analog audio signals from a microphone. These analog audio signals are converted to digital signals and encoded by Baseband 620. Baseband 620 also codes the digital signals for transmission and generates a baseband transmit audio signal that is routed to the modulator portion of Radio 615. The modulator mixes the baseband transmit audio signal with an RF carrier signal generating an RF transmit signal that is routed to the antenna system and may pass through a power amplifier (not shown). The power amplifier amplifies the RF transmit signal and routes it to Antenna 610 where the signal is switched to the antenna port for transmission.

Baseband 620 is also communicatively coupled with Processor 560. The central processing unit, Processor 560, has access to the data storage areas, Main Memory 565 and Secondary Memory 570. The central processing unit, Processor 560, is configured to execute instructions (i.e., computer programs or software) that can be stored in Main Memory 565 or Secondary Memory 570. Computer programs can also be received from the baseband processor, Baseband 610, and stored in Main Memory 565 or in Secondary Memory 570, or executed upon receipt. Such computer programs, when executed, enable System 550 to perform the various functions as previously described. For example, Main Memory 565 may include various software modules (not shown) that are executable by Processor 560.

Figure 6:
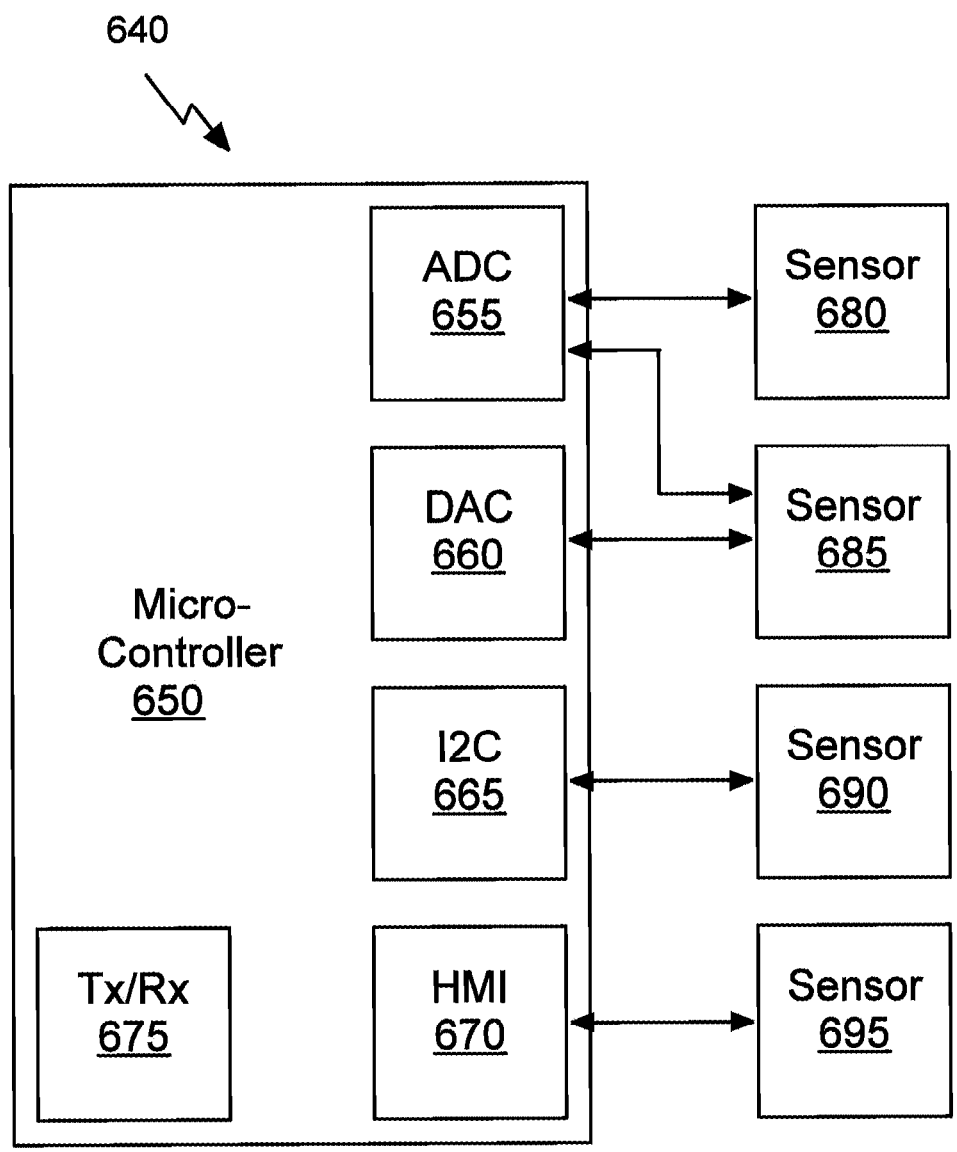
FIG. 6 illustrates an example of a sensor platform.

FIG. 6 is a block diagram illustrating an embodiment of a wireless system 640 that may be used in connection with the various embodiments described herein. For example System 640 may be used to implement Sensor 140 as described with respect to FIG. 1, as well as Sensor 250, as described with respect to FIG. 2. In some embodiments, System 640 may comprise a Microcontroller 650, which may offer integrated functions such as an analog-to-digital converter ADC 655, a digital-to-analog converter DAC 660, an Inter-Integrated Circuit interface I2C 665, a Human-Machine Interface HMI 670, and a transceiver Tx/Rx 675. In various embodiments, Microcontroller 650 may be implemented using a microcontroller manufactured by Freescale Semiconductor, Inc., such as the Freescale Kinetis KW01.

Figure 7:
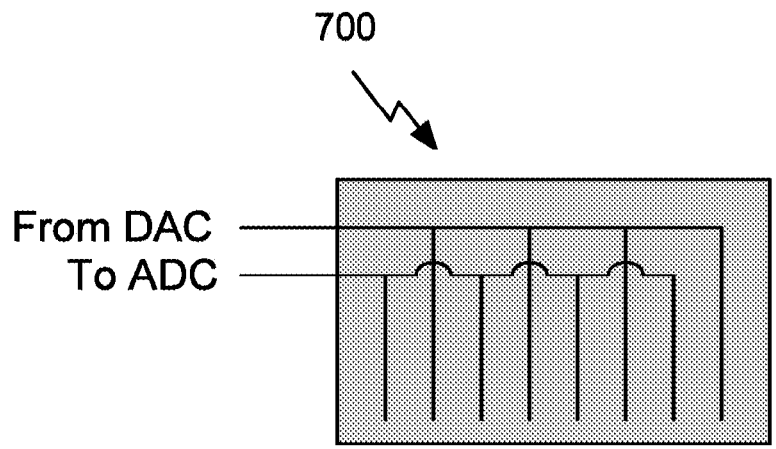
FIG. 7 illustrates an example of a sensor component for measuring the resistance of a soil.

In some embodiments, System 640 may also include one or more sensors, such as Sensor 680, Sensor 685, Sensor 690, and Sensor 695. For example, Sensor 680 may output a voltage based on a measurement of temperature, pH, or light. In some embodiments, ADC 655 may measure the voltage supplied by Sensor 680, after which Microcontroller 650 may determine the soil temperature, soil pH, or ambient light based on the voltage measurement. As another example, Sensor 685 may be comprised of a PCB 700 as shown in FIG. 7, wherein PCB 700 may be composed of interleaved traces on the PCB. The first set of traces may be connected to DAC 660 to receive a specified voltage and a second set of traces, which are not connected to the first set of traces as shown by the rounded hop-overs, may be connected to ADC 655 and a resistor of known value connected to ground. Based on the voltage applied by DAC 660 and the voltage measured by ADC 550, Microcontroller 650 may determine a soil resistance based on the voltage difference between the applied and measured voltages. In some embodiments, the applied voltage may be stepped across a range of voltages, thereby extending the dynamic range of ADC 655.

As another example, Sensor 690 may also use an off-the-shelf temperature or humidity measurement component that can communicate with Microcontroller 650 via I2C 665.

As another example, a touch sensor is designed to accurately read small capacitive changes induced by skin contact with a capacitive touch screen. HMI 670 may also use such a touch sensor, except HMI 670 may be connected to Sensor 695 that contains capacitive plates in contact with soil rather than a touch screen. By measuring the capacitance of such plates in Sensor 695 at different frequencies via HMI 670, Microcontroller 650 may determine a soil's dielectric constant. In various embodiments, Microcontroller 650 may further determine the soil's moisture content using the soil's dielectric constant, salinity, and methods known in the art.

In various embodiments, System 640 may use well-known methods in the art to support multiple sensors as described above, such as by using multiplexers/demultiplexers. Accordingly, in various embodiments, numerous sensors for different measurements may be connected to ADC 655, DAC 660, I2C 665, or HMI 670 and the use of ADC 655, DAC 660, I2C 665, or HMI 670 for obtaining measurements from one sensor does not preclude ADC 655, DAC 660, I2C 665, or HMI 670 from being used for obtaining measurements from another sensor. By using such methods well known in the art, System 640 may determine a parameterized measurement of a soil's salinity, pH, and evaporation rates based on measurements of a soil's resistance, capacitance, pH, and temperature as well as other measurements such as measurements of ambient light, air temperature, and air humidity.

In various embodiments, System 640 may transmit the measurements from various sensors as described above to a cloud platform (e.g., Cloud Platform 110, Cloud Platform 210). The cloud platform may perform the same analysis, calibration, or other adjustments to the measurements as described herein with respect to System 640. In some embodiments, an intermediate component, such as Hub 240, Device 181, Device, 182, Device 291, or Device 292, may also perform analysis, calibration, or other adjustments based on the measurements described herein with respect to System 640. By using such methods well known in the art, the cloud platform or intermediate components (e.g., Hub 240, Device 181, Device, 182, Device 291, or Device 292) may determine a parameterized measurement of a soil's salinity, pH, and evaporation rates based on measurements of a soil's resistance, capacitance, pH, and temperature as well as other measurements such as measurements of ambient light, air temperature, and air humidity. In various embodiments, the cloud platform or intermediate components (e.g., Hub 240, Device 181, Device, 182, Device 291, or Device 292) may then transmit results of the above analysis to System 640 or other components described herein. For example, System 640 may receive instructions to adjust future measurements based on analysis, calibration, or other adjustments from the cloud platform or intermediate components (e.g., Hub 240, Device 181, Device, 182, Device 291, or Device 292).

In some embodiments, Microcontroller 650 may also include TX/RX 675. In such embodiments, TX/RX 675 may be an IEEE 802.15.4-compliant device that has the ability to adjust its data rates and transmitter power using measurements of received signal strength from other transmitting devices. In various embodiments, TX/RX 675 may use other wireless methods such as ZigBee, Bluetooth, or Wi-Fi.

Figure 8:
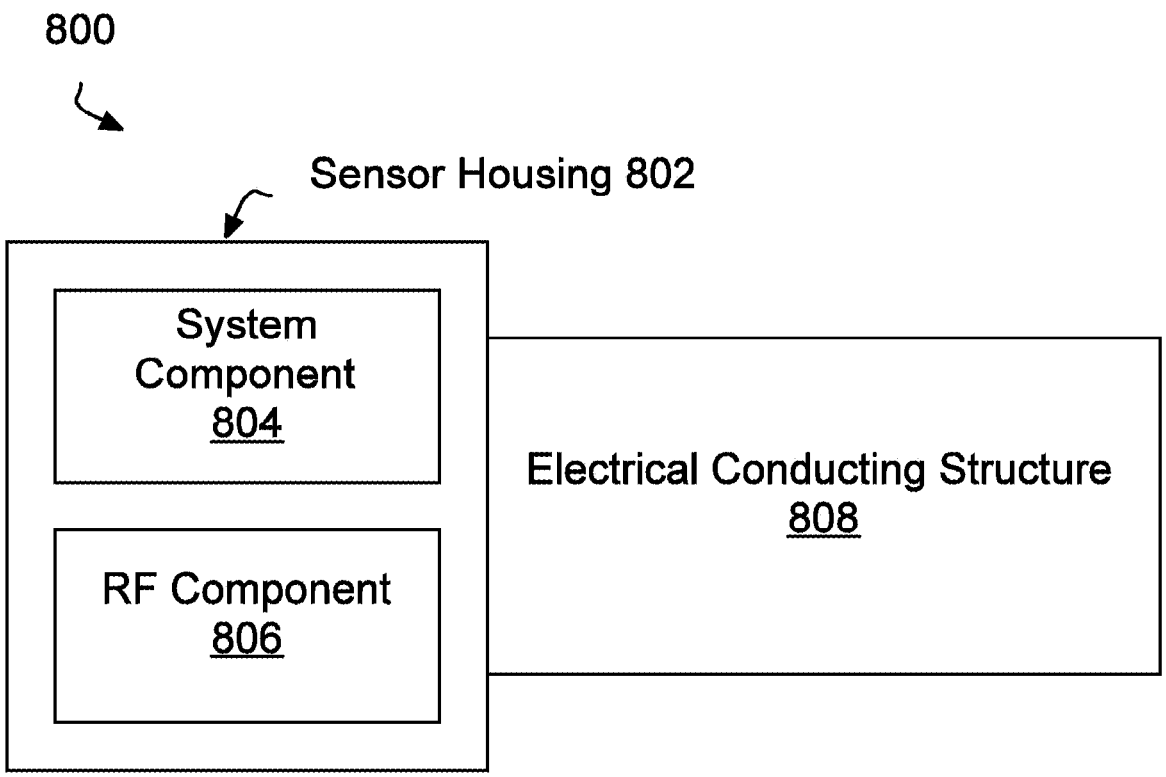
FIG. 8 illustrates an example of an embodiment for collecting garden parameters.

FIG. 8 is a diagram illustrating an embodiment of a System 800 for collecting garden parameters, which is an improvement on the system disclosed in U.S. Pat. No. 5,479,106 to Campbell. As shown in FIG. 8, in some of the embodiments described herein, System 800 may comprise a Sensor Housing 802, which may contain a System Component 804 and an RF Component 806. Further, Sensor Housing 802 may provide a physical and electrical interface between Electrical Conducting Structure 808 and System Component 804. Sensor Housing 802 may shield the sensitive electronics of System Component 804 and RF Component 806 from water, other contaminants, and mechanical or electrical damage. In some embodiments, the interior of Sensor Housing 802 may be filled with a solid or gelatinous compound to provide resistance to shock and vibration or for the exclusion of moisture or other corrosive agents.

System Component 804 may contain electronics that may be used to make basic electrical measurements for determining soil properties or to transmit data to a data collection platform. In some embodiments, System Component 804 may also contain electronics that may be used to receive data from a data collection platform. System Component 804 may be coupled to Electrical Conducting Structure 808. Electrical Conducting Structure 808 may form a capacitive element when placed in soil, thereby allowing System Component 804 to measure the soil electrical characteristics via Electrical Conducting Structure 808. In some embodiments, Electrical Conducting Structure 808 may be a capacitive touch sensor. In other embodiments, Electrical Conducting Structure 808 may be two or more metal strips slightly separated from each other.

RF Component 806 may contain internal batteries, a radio, and an antenna for transmission and reception of data between System Component 804 and a data collection platform. In some embodiments, RF Component 806 may use a multi-conductor wire to power itself and System Component 804 instead of using internal batteries.

Figure 9:
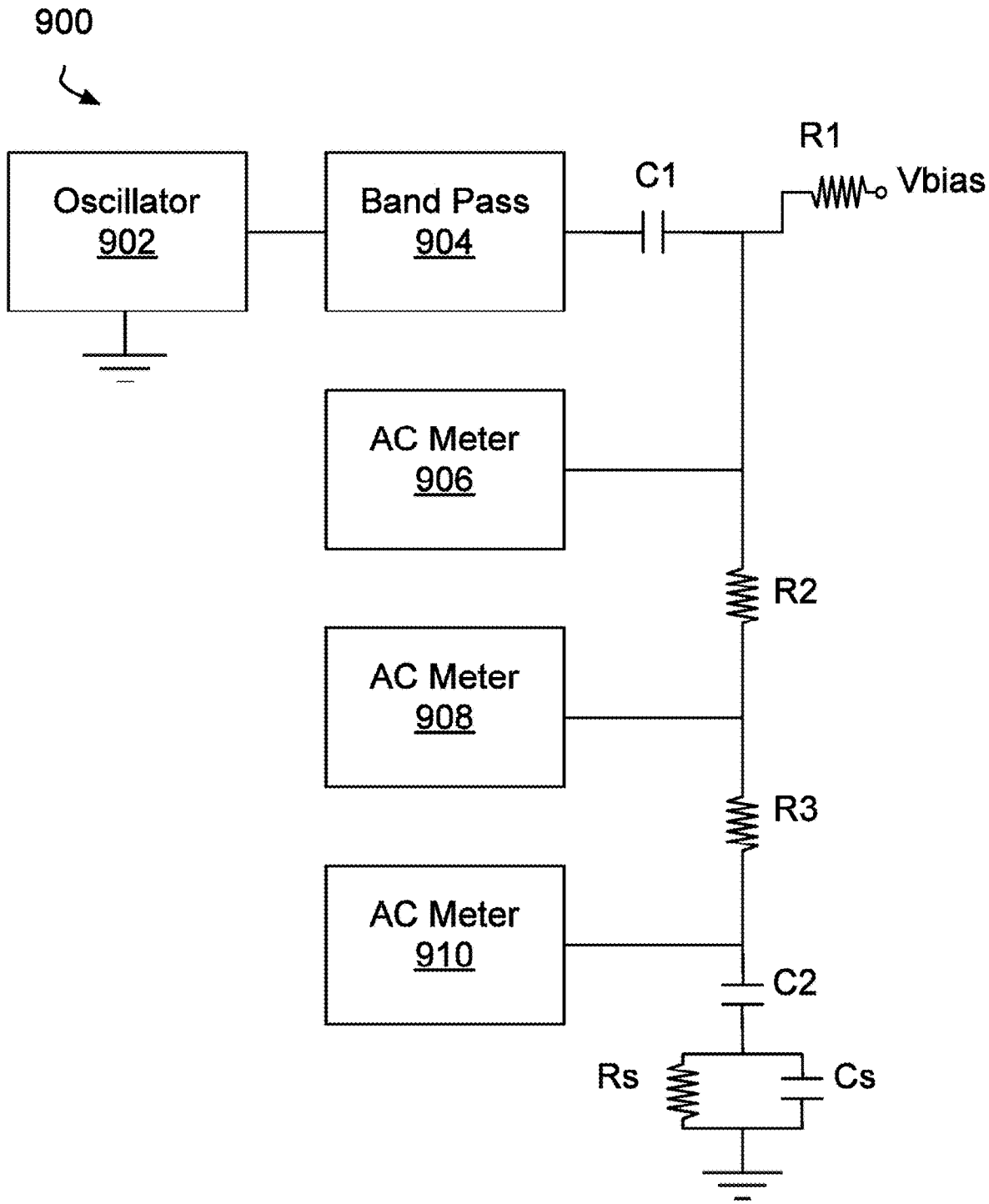
FIG. 9 illustrates an example of an embodiment for performing sensor measurements.

FIG. 9 is a diagram illustrating an embodiment of a System 900 for performing sensor measurements within System Component 804. As shown in FIG. 8, Oscillator 902 may be coupled to a Bandpass Filter 904. Oscillator 902 may be used to apply a high frequency electrical signal (e.g., 10 to 200 MHz) to the Bandpass Filter 904. In some embodiments, the oscillator may be a simple square-wave clock oscillator and Bandpass Filter 904 may then be used to eliminate the higher order harmonic frequencies to form a sinusoidal signal. In other embodiments, Oscillator 902 may be a different type of oscillator (e.g., sine-wave) and Bandpass Filter 904 may be used to eliminate any undesirable frequency components or omitted. The output of Bandpass Filter 904 may then be applied to a capacitor C1, which may act as a blocking capacitor to filter out any undesirable DC component in the signal output of Bandpass Filter 904.

In some embodiments, a bias voltage may be applied at Vbias across R1 (shown in FIG. 9) for facilitating sensitive analog measurements. The output of R1 and C1 may then be combined and coupled to the input of AC Meter 906 and the input of R2. The output of R2 may then be coupled to the input of AC Meter 908 and the input of R3. The output of R3 may then be coupled to the input of AC Meter 910 and capacitor C2. In such embodiments, AC Meters 906, 908, and 910 along with resistors R2 and R3 may be understood to form a sensitive bridge circuitry that may facilitate measuring differences, as explained below, in the amplitude of an AC electrical signal originally generated by Oscillator 902. Capacitor C2 may also act as a blocking capacitor to prevent any DC component from the bias voltage passing to Electrical Conducting Structure 808. This may be necessary where such a DC component may cause galvanic corrosion of the conducting structure in the presence of the soil or where such a bias voltage would distort measurements if applied to Electrical Conducting Structure 808. Capacitor C2 may then be connected to Electrical Conducting Structure 808, which may be represented as a resistor Rs and capacitor Cs in parallel, so that the AC signal is applied to Electrical Conducting Structure 808.

Figure 10A:
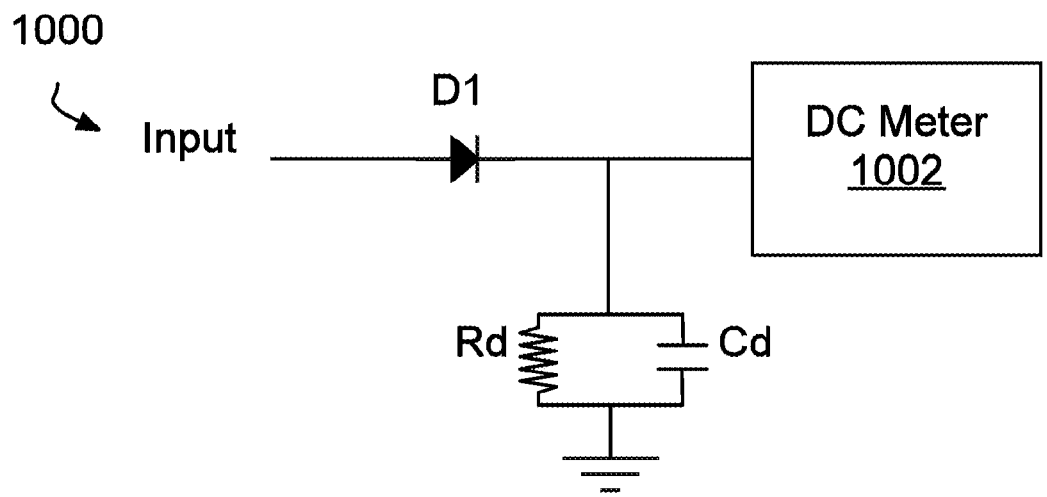
FIG. 10A illustrates an example of a system for measuring AC signals using DC meters.
Figure 10B:
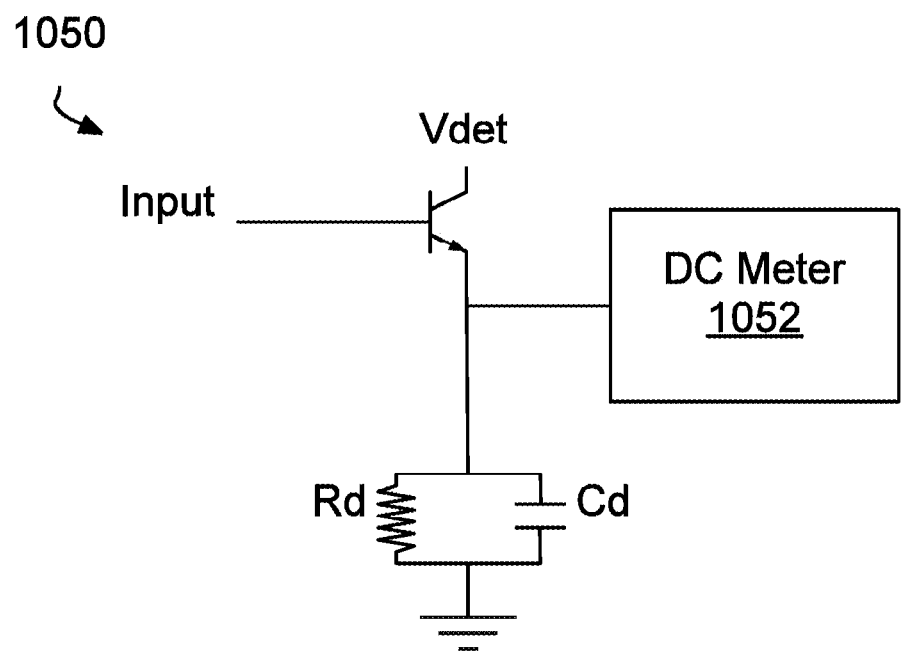
FIG. 10B illustrates another example of a system for measuring AC signals using DC meters.

In various embodiments, DC meters may be used instead of AC Meters 906, 908, and 910, such as where the cost of accurate AC Meters would be too high. FIGS. 10A and 10B show diagrams of two such approaches for using DC meters instead of AC meters to measure AC signals.

With respect to FIG. 10A, System 1000 is shown for measuring AC signals, which may use a DC Meter 1002, a diode D1, a resistor Rd, and a capacitor Cd. In such an embodiment, if an AC signal is applied to diode D1, only the positive component of the AC signal may pass through diode D1. This filtered AC signal may then be applied to the RC circuit that uses Rd and Cd to create a filtered DC signal that may be measured by DC Meter 1002. In such an embodiment, the amplitude of the DC signal may correspond to the amplitude of the AC signal that was applied to the input of diode D1.

With respect to FIG. 10B, an alternative System 1050 is shown for measuring AC signals, which may use a DC Meter 1052, a transistor T1, a resistor Rd, and a capacitor Cd. In such an embodiment, if an AC signal is applied to transistor T1, only the positive component of the AC signal may pass through transistor T1. This filtered AC signal may then be applied to the RC circuit that uses Rd and Cd to create a filtered DC signal that may be measured by DC Meter 1052. In such an embodiment, the amplitude of the DC signal may correspond to the amplitude of the AC signal that was applied to the input of transistor T1.

In such embodiments as shown in FIGS. 10A and 10B, a bias voltage may need to be combined with the AC signal to facilitate the accurate measurement of the AC signal. For example, biasing the AC signal may dramatically improve the linearity of the signal applied to the DC meters or allow for much smaller AC signal levels to be measured.

Figure 11:
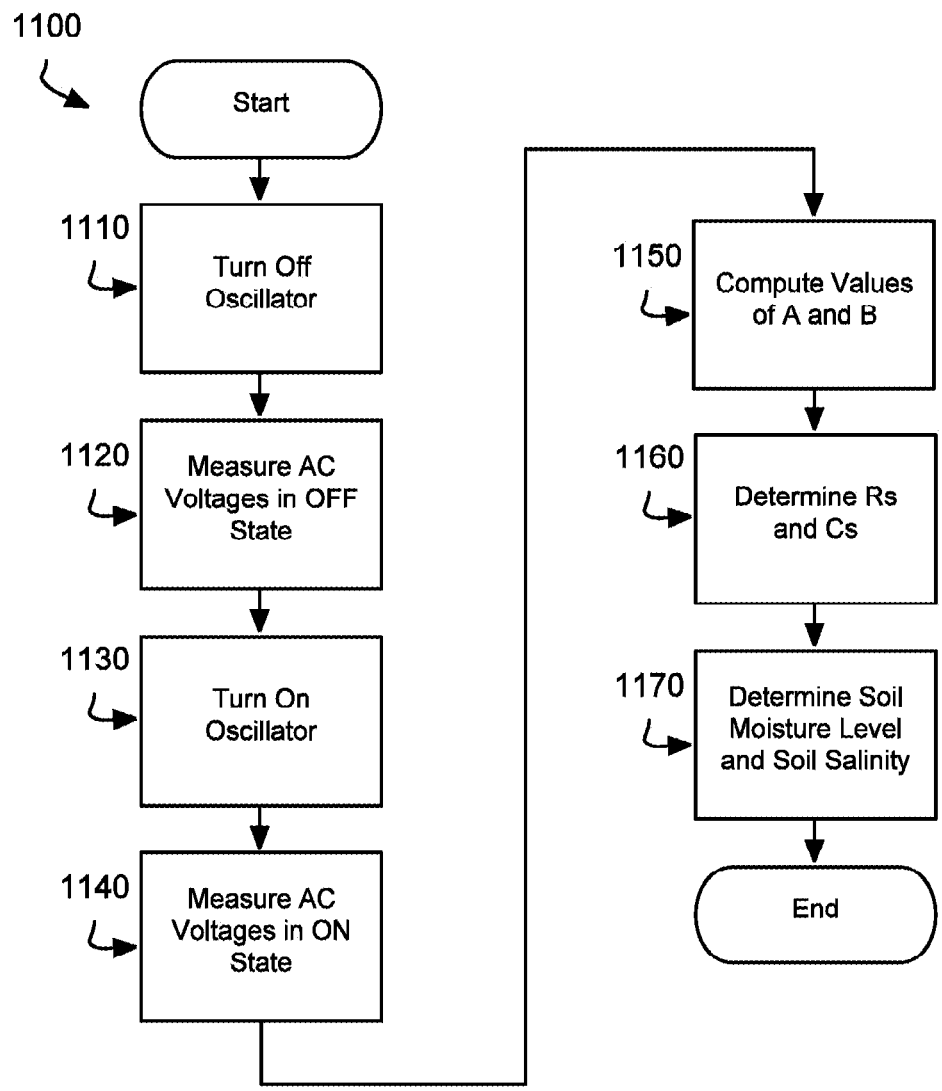
FIG. 11 describes a method for measuring soil characteristics

With respect to FIG. 11, a Method 1100 is shown for measuring soil characteristics. At step 1110, Oscillator 902 may be turned off. At step 1120, measurements of voltages Voff1, Voff2, and Voff3 may be respectively recorded by AC Meters 906, 908, and 910. At step 1130, Oscillator 902 may be turned on. At step 1140, measurements of voltages Von1, Von2, and Von3 may be respectively recorded by AC Meters 906, 908, and 910. At step 1150, the values of A and B may be computed as follows: A=(Von2−Voff2)/(Von1−Voff1) and B=(Von3−Voff3)/(Von1−Voff1). At step 1160, Cs and Rs may then be computed based on the known values of R2, R3, A, and B, such as by the method shown in U.S. Pat. No. 5,479,106. At step 1170, soil moisture level and soil salinity may be determined based on Rs and Cs using methods known in the art.

Taking measurements of voltages with the improved bridge circuit shown in FIG. 8 using AC Meters 906, 908, and 910 when the oscillator is both on and off as described by Method 1100 may reduce measurements problems relating to temperature dependence in the meter output, avoid the need for taking into account varying diode forward voltage drop when calculating values A and B in step 1150, and allow for lower cost components to be used as compared with techniques known in the art.

Wireless Telemetry

Hostile radio environments (lossy media, widely varying media, etc.), such as soils, cement, human or animal tissue, building materials, water including seawater, and other media, may pose a distinct challenge to traditional RF telemetry in that they may strongly attenuate RF energy, and thus dramatically reduce communication range as well as making transmit/receive antenna design difficult. In addition, in media with widely varying electrical properties such as soil, an antenna that is an efficient radiator under one condition, may be a very poor radiator if the soil moisture or salinity changes. One embodiment for resolving these problems may operate using "near field" principles by implementing an oscillating electrical stimulus at a frequency such that the electromagnetic wave in the medium is much larger than the transmitting and receiver structure sizes as well as the separation between them.

To address one or more of the problems associated with such electromagnetic-absorbing materials, a wireless sensing system has been developed that is suitable for long-term placement within an electromagnetic-absorbing material (e.g., underground). While the system is described herein using a buried soil moisture sensor for agricultural applications, the system may be applicable to numerous other applications including, but not limited to, monitoring of concrete curing, underwater sensing, etc. Thus, the material may be soil, rock, water, concrete, and combinations thereof (e.g., soil underneath a concrete roadway or walkway, below water table saturated soil, various building materials, etc.). Such electromagnetic-absorbing material present challenges to traditional propagated wave communications techniques (e.g., cellular, WiFi®, Bluetooth®, etc.)

Figure 12:
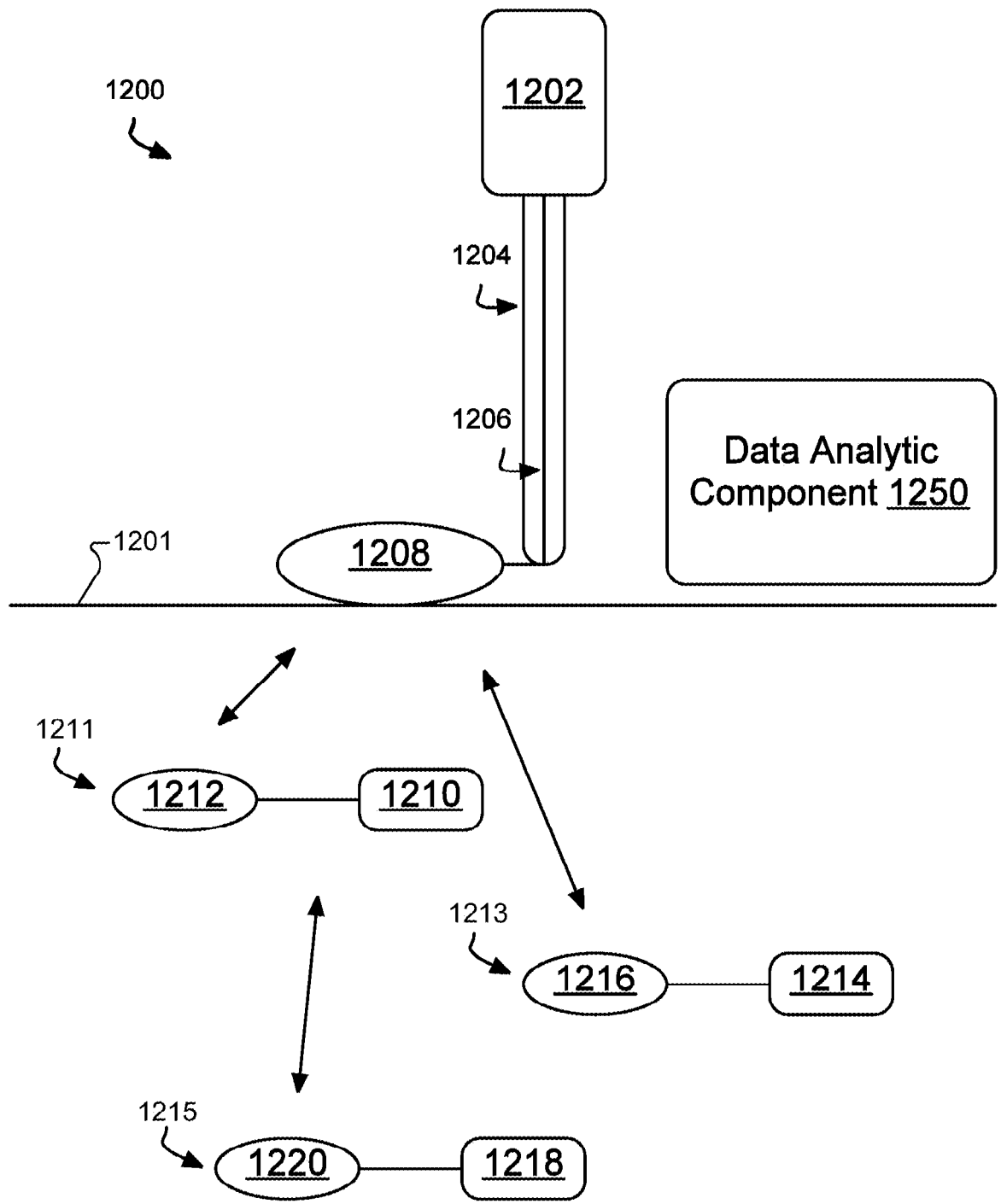
FIG. 12 shows an example of an application for soil monitoring.

With respect to FIG. 12, an application of such a System 1200 for soil monitoring is shown. System 1200 may use a Receiver 1202 connected by Cable 1206 to Transmit/Receive Structure 1208. As shown in the example, Receiver 1202 may be elevated above ground level 1201, such as by use of Pole 1204, to protect the electronics from environmental factors or other concerns. System 1200 may also use one or more Sensors (e.g., 1211, 1213, 1215) positioned below ground level 1201 (e.g., embedded within soil) that may each include Sensing elements 1210, 1214, 1218 respectively coupled to a Transmit/Receive Structure (e.g., 1212, 1216, 1220). In alternative embodiments, the Receiver can incorporate the Transmit/Receive Structure.

In some embodiments, Receiver 1202 may be located (typically at distances less than 5 m or so) near Sensors 1211, 1213, and 1215. In such an arrangement, if the Transmit/Receive Structure 1212, 1216, 1220 of any of the Sensors 1211, 1213, 1215 are transmitting, then an electrical signal may be produced in Receiver 1202's receiver structure which may then be demodulated to recover the data transmitted by the Sensors 1211, 1213, 1215. Receiver 1202 may use this same receiver structure, or a separate transmit structure, to communicate with the Sensors 1211, 1213, 1215. In various embodiments, the arrangement may include additional receivers and sensors distributed over a geographic area.

Receiver 1202 may typically include a power source, such as batteries, solar power, a utility connection, or some other power source. The Receiver may be fixed in place or mounted onto mobile equipment such as drones, equipment such as tractors, combines, center pivots, or other devices that move over an area that is to be monitored. In addition, Receiver 1202 may have memory to store data as well as an additional radio, such as a cellular modem, a 934 MHz telemetry radio, a direct connection to the Internet through a Wi-Fi router or Ethernet, or other means of communicating collected sensor data to a network. By including such an additional radio, various embodiments may allow for remote monitoring of collected data and system operating parameters, as well as potentially reconfiguring the system's monitoring performance or software.

Sensors 1211, 1213, 1215 may be buried in the soil and may each be equipped with a Transmit/Receive Structure (e.g., 1212, 1216, and 1220). Transmit/Receive Structures 1212, 1216, or 1220 may use a coil of one or more turns that may be electrically insulated from the soil, which may be tuned with additional capacitors to form a resonant structure at a desired drive frequency. In addition, such coils may incorporate a ferrite or other material of high magnetic permeability to enhance a generated magnetic field. Such wire coils may be driven with an electrical current at a desired frequency with a suitable modulation scheme so as to encode a sensor identification code, sensor operating parameters such as battery level, and any data measured by Sensing elements 1210, 1214, or 1218. If such Sensors 1211, 1213, 1215 are placed in soil, such data may include one or more parameters such as soil moisture, salinity, and temperature. In addition, the Transmit/Receive Structures 1212, 1216, and 1220 of Sensors 1211, 1213, or 1215 may use the same transmitting structure, or a separate structure, to receive information, trigger measurement, update sensor firmware, change operating parameters, or facilitate location of Sensors 1210, 1214, or 1218 by allowing the Transmit/Receive Structures 1212, 1216, and 1220 to act as a transponder. Sensors 1211, 1213, or 1215 may each use a power source such as a battery, a microcontroller, circuitry used to make one or more desired measurements, and circuitry to drive and modulate/demodulate the transmitting/receiver structure.

In some embodiments, a Data Analytic Component 1250 may be included in System 1200. Data Analytic Component 1250 may reside on a server or at one or more Receivers 1202 of System 1200. Data Analytic Component 1250 may process incoming sensor data to provide management decisions and possibly implement control operations, such as turning on irrigation managing irrigation efficiently with respect to peak electrical power costs, scheduling agricultural operations such as spraying, tilling, etc. to reflect the actual conditions. In addition, Data Analytic Component 1250 may adapt System 1200 based on incoming data to reconfigure sensing to acquire enhanced information about the area being monitored.

For example, in the case of agriculture, water infiltration rates provide key information as to the most efficient irrigation strategies, plant health, and whether cultural practices such as deep tilling are indicated. A fixed interval soil moisture sensing approach may be optimal for battery life management in routine monitoring, but may be otherwise insufficient to capture the dynamic changes in soil moisture that occur when irrigation is in progress. To capture these events and better characterize the site, the System 1200 may increase the frequency of soil moisture measurement acquired by one or more of the Sensors 1211, 1213, 1215 and data transmission by one or more of the Sensors 1211, 1213, 1215 to the Receiver 1202. This enhanced frequency data can then be used to derive better estimates of water infiltration rates.

The communication link between a Receiver 1202 and a Sensor (e.g., 1211, 1213, 1215) in System 1200 may depend on near field interactions between the transmitting and receiving structures. In one implementation, these structures may be wire loops including one or more turns of insulated wire. They may also incorporate tuning inductors/capacitors to form a resonant structure at the intended operating frequency, which has the advantage of decreasing the required drive level in the transmitter, increasing the receiver sensitivity at the operating frequency, and suppressing noise at other frequencies. In addition, the coils may incorporate ferrites or other high permeability materials to enhance the transmitted and received signals. Other possible implementations include simple electric dipole antennas that use linear meandering wires, but magnetic wire loops have significant advantages.

An oscillating electrical current in the transmitting coil of a transmit/receive structure may produce an oscillating magnetic field that intersects with the receiving coil. This may then produce an oscillating current in the receiving coil through induction that may then be detected by the Receiver 1202 in System 1200. As such, if a transmitting coil current is modulated, a receiving coil may have a similarly modulated current. In such a situation, by using a suitable modulation scheme (e.g., amplitude modulation) may allow the Receiver 1202 to recover Sensor data. The process may also be reversed to allow a Receiver in System 1200 to communicate with a Sensor in System 1200.

Figure 13:
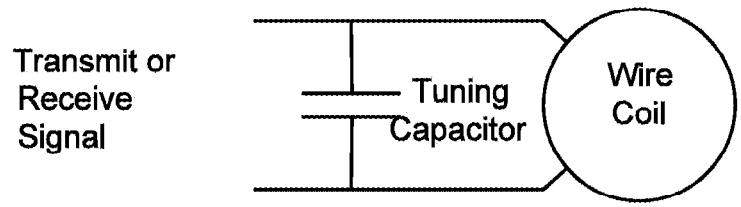
FIG. 13 shows an example of a transmission or receiving coil structure.

With respect to FIG. 13, an example of a wire coil connected to a tuning capacitor is shown that may be used as a transmitting or receiving structure in System 1200. The drive frequency when used as a transmitting loop may be varied from a few kHz up to a few MHz with the only restriction being that the transmit and receive coils have a total length for each coil that is much smaller than a quarter wavelength of the drive frequency. As such, at 3 MHz total coil lengths can be as much as 10 m, while at 100 kHz, they can be very long-up to a few hundred meters.

While range may be much more limited in System 1200 than when compared with traditional RF telemetry approaches, the shorter range and very low fields in the far field may allow for unlicensed FCC operation by providing operation within the radiated field strength limits specified in the FCC regulations.

The typically short communication range (e.g., 10 m or less) may also allow for simple radio protocols to be implemented in a Receiver of System 1200, as it may reduce the possibility of transmissions from distant Sensors in System 1200 interfering with Sensors in System 1200 that are closer to the Receiver.

Drive circuitry for a transmitting structure as shown in FIG. 13 may be as simple as using a low frequency microcontroller I/O port output to drive the transmit coil. Such an approach may also be used to reduce transmission power consumption, thereby extending battery life.

If the communication range of a Sensor in System 1200 is under 10 m, a Receiver in System 1200 may be placed near such a Sensor. However, if Sensors are buried or in other intervening media, their location may not be visually apparent. In some applications such as monitoring structures or other forms of construction, the locations of such Sensors may be readily marked. In many agricultural settings, though, this is not easily achieved as fields are often tilled through the use of heavy equipment, thereby making the use of flagging or other Sensor markings unattractive due to the potential of accidental damage. Thus, in such situations, it may be desirable to allow the removal of Receivers in System 1200 from the field when the field is either fallow or when intensive cultural operations occur such as tilling, harvesting, spraying, etc.

Figure 14:
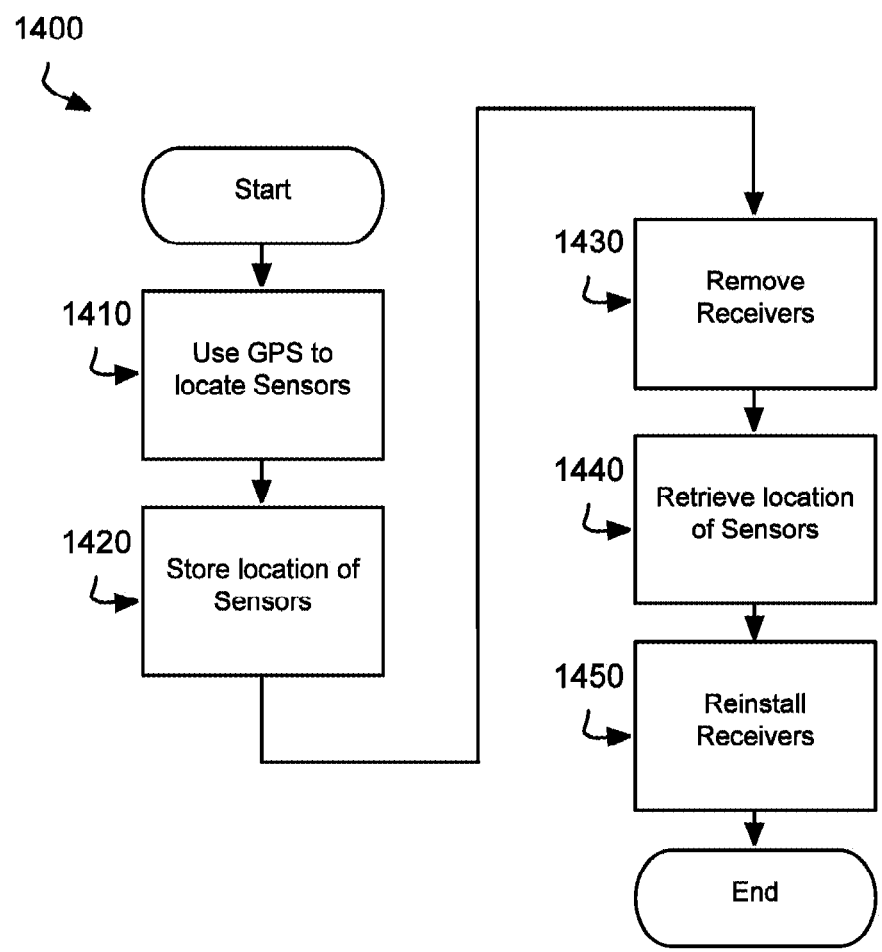
FIG. 14 describes a method for tracking sensor locations.

With respect to FIG. 14, a method 1400 is shown for tracking sensor locations. At step 1410, at the time of system install, a differential GPS system may be used to reliably locate the Sensor placement to within a few centimeters by placing a GPS base station at a known location on a site, such as a farm, and using a roving GPS receiver during the install. At step 1420, the locations of Sensors and Receivers in System 1200 may be stored in a database. At step 1430, the Receivers in System 1200 may then be removed from the field (while leaving the Sensors of System 1200 buried). At step 1440, the locations of Sensors and Receivers in System 1200 may be retrieved at the time of redeployment. At step 1450, the Receivers in System 1200 may then be reinstalled to within a few centimeters of their original positions.

Method 1400 may be made more convenient by using a mobile phone application. Such an application may possibly be a bar code reader in communication with the GPS roving unit via Bluetooth or other short range wireless communication, thereby allowing for a quick and easy installation of Sensors in System 1200 and recording of their location in a database. For example, a Sensor or Receiver in System 1200 may be scanned by the bar code reader, then installed in its location, and then the GPS roving unit is positioned in place, and the user hits a "capture" sequence that then combines the location with the unit serial number and can then populate a database with the location of a Sensor or Receiver based on its bar code.

In other embodiments, if Sensors in System 1200 have both transmit and receive functionality (e.g., Transmit/Receive structures 1212, 1216, 1220), then various methods known in the art may be used to store a rough location of the Sensors in a database (e.g., non-differential simple GPS, sighting lines, or by triangulating distances from fixed, prominent locations to get within 5-10 m of the Sensor). A field unit may be used transmit a steady beacon of commands the Sensor may be capable of receiving, which may then be used to trigger a responding transmission from the Sensor, thereby allowing one to systematically scan an area and estimate the Sensor's precise location. As with differential GPS, a mobile application can greatly facilitate this process.

In some configurations of System 1200, it may be possible to mount Receivers on moving structures such as center pivots, lateral irrigation lines, field equipment such as tractors, combines or other vehicles. In such configurations, Sensors with receive capability may be interrogated by a Receiver and triggered into making a measurement and sending the collected data. As such, roving vehicles such as vehicles, tractors, and drones may be used to collect the data by moving to the Sensor location, issuing a command to cause the Sensor to make a measurement, receiving the message (and either storing it for future download or sending via an alternative communication approach such as a cellular modem).

As another example of specific adaptation of System 1200, a center pivot may be equipped with one or more Receivers along its irrigation line, which then may move in known, repeatable paths across a field. The rate of motion of these structures is generally quite slow (roughly of the scale of 1 meter per minute). This may allow a Sensor to make measurements and transmit the results based on the transmission range of the Sensor and the speed of the structure. For example, if the range of a Sensor is 5 m and a center pivot moves an irrigation line at 1 meter per minute, the Sensor may be instructed to transmit at intervals of slightly under 10 minutes. When the center pivot stops, it may be placed in a location near numerous Sensors to allow for collecting data from a limited number of Sensors.

To transmit information from the Sensor to the Receiver (or vice-versa) a communication protocol may be implemented. While parallel communication schemes may be utilized, in some embodiments data may be sent using standard asynchronous schemes using an idle period to separate data packets, and a transition to mark the data packet start, followed by a data packet, and any error checking protocol, and a stop bit followed by another idle period marking the end of the packet. Both Sensors and Receivers in System 1200 may have local clock signals accurate to within better than 5% which may allow appropriate time-framing of the received signals. Possible modulation schemes include phase, amplitude, or frequency shift keying.

In noisy environments, particularly when using Sensors in System 1200 without a receive capability, the detection, as well as correction, of errors is desirable. This may be implemented using simple parity bits to detect a single bad bit or involve more sophisticated forward error correction routines.

In some embodiments, Sensors in System 1200 may use a dynamic Sensor data transmission scheme to only sends data packets only if specific criteria have been met since the last Sensor transmission. Criteria that may be implemented include only sending transmissions when there has been a significant change in one or more measured values since the last transmission, a threshold in one or more values has been breached, etc. This may allow the Sensors in System 1200 to sample more frequently but only transmit values when the measured properties are changing. This can help conserve power on Sensors as well as Receivers in System 1200. For example, a Sensor in System 1200 with soil moisture measurement capability may be programmed to measure soil moisture once every minute, but only to transmit data if the soil moisture change exceeds a threshold. This approach allows such a Sensor to transmit data at frequent intervals during periods of dynamic change in soil moisture (such as during irrigation events) so as to determine important information about water percolation rates, while simultaneously suppressing redundant transmission of data during static soil moisture conditions. In some embodiments, the criteria used to determine whether to send a transmission or not may include a requirement to always transmit a packet at least once in a specified time interval. This may be necessary where a lack of communication from a Sensor in System 1200 may be interpreted as a Sensor that is no longer in operation.

In some embodiments, when more than one Sensor is deployed within communication range of a Receiver in System 1200, Sensor transmissions may need to be identified by the particular Sensor that sent the transmission. This may be implemented by giving each sensor a unique serial number. If the Sensor transmit range is small in System 1200 (e.g., a few meters), an abbreviated Sensor identifier may be used to resolve which Sensor transmission corresponds to which physical Sensor. For example, a small 4-bit identifier may be used to identify 16 different Sensors within range of one Receiver in System 1200. A mobile application may also be used to verify that for each Receiver in System 1200, no duplicates in the 4-bit identifier occur within the range of said Receiver. Additionally, Sensors in System 1200 may be configured to periodically, such as at infrequent intervals, to transmit the short identifier along with a full serial number, which may allow a Receiver in range to associate the unique Sensor serial number with the short identifier.

In other embodiments, particularly those with Sensors having a transmit only capability, if Sensors report at fixed time intervals in System 1200, a Sensor may occasionally move into synch with another Sensor as their local time keeping clocks drift. In order to avoid repeated transmissions colliding, a fixed reporting interval may be varied by a small pseudo-random time. This may be based on adding or subtracting a random time small compared to the transmit interval. This random number may be generated in a number of ways including using the Sensor serial number to generate a random number sequence.

In embodiments where Sensors in System 1200 have a receive capability, the Receivers may time synch the Sensor response times so that each Receiver can be in a low power state except during Sensor transmissions. In addition, a Receiver in System 1200 may modify the Sensor(s) reporting interval or other behavior in response to system-wide operating conditions that are communicated to the Receiver, such as via an external network interface. For example, when crops are fallow, the Receiver may be informed of this state, and then direct itself, as well as the Sensors connected to it into a very low power, sparse reporting mode to conserve battery life during these periods when irrigation is not occurring. In further embodiments, a Receiver in System 1200 may monitor a Sensor transmission signal level and error rate (when employing FEC or parity bits) and if the signal is too low or noisy, such a Receiver may direct a Sensor to increase transmit power levels or use stronger error correction techniques.

To conserve power on a Receiver in System 1200 and to facilitate long battery life or allow operation with small solar power panels, in some embodiments a low power scheme may be implemented using a very low power transmission detection circuit. In such embodiments, while waiting for Sensor transmissions, only the low power transmission detection circuitry may be powered in a Receiver of System 1200. A Sensor may then transmit a simple, short "wake-up" signal that the Receiver may then detect and use to wake up the full Receiver circuitry. A short interval after a Sensor issues the "wake-up" signal, a full Sensor transmission may occur. After receipt of this Sensor transmission, the Receiver may either store the packet for later transmission or send it via a network interface, and then return to the very low power mode.

In such embodiments, if the Sensors of System 1200 have a receive capability, the Receiver may use synch signals to schedule Sensor transmission into known windows, thereby allowing the Receiver to be in a low power mode except during these short Sensor reception windows. The Receiver may periodically resynch the Sensors in order to correct for time keeping errors in the Sensor and Receivers.

In further embodiments, a Receiver in System 1200 may be used to prioritize data transmissions via its network interface depending on preset algorithms. For example, such a Receiver may only be instructed to send summary data, such as statistics showing just the high and low readings over a time interval or other condensed metrics. In addition, depending on user configuration or management operations, the frequency and detail of the data that is sent by such a Receiver via its network interface may be modified. For example, during irrigation operations, instructions may be followed that require such a Receiver to send the full Sensor data at short intervals so as to provide better data that allows for determining optimum irrigation run times.

As an example of specific embodiment of System 1200, a group of 10 Receivers may be distributed over a 400-acre farm. Each Receiver may be installed near 12 Sensors buried in the soil that are capable of measuring soil moisture, salinity, and temperature. The Sensors may be transmit-only sensors employing a 4 bit identifier, and a 4 byte sensor measurement packet. The operating frequency of the Sensors may be 173 kHz with a 1200 baud transmit rate using an asynchronous amplitude shift key modulation. Simple FEC employing a Hamming 7,4 scheme capable of detecting one or two bit errors and correcting a single bit error may be employed. The total Sensor packet with FEC of such an arrangement if employed is approximately 10 bytes occupying about 0.2 s of transmit time.

The Sensors may be set to measure soil moisture, salinity, and temperature at 2 minute intervals and transmit current readings at least once every 20 minutes or if any measured value changes by more than a preset limit since the last Sensor transmission. The Sensors may also transmit a short "wake-up" signal to the Receivers 0.2 s before actual Sensor data transmission begins.

The Receivers may be battery powered with low power "wake-up" signal detection circuitry to monitor the 173 kHz Sensor transmissions. Generally, the Receivers may be in a low power mode monitoring for a "wake-up" signal and then switch into a more power intensive receive mode. The Receivers may have sufficient memory to allow up to one month of Sensor data to be stored on the Receiver and may have a cellular modem for uplink to Data Analytic Component 1250, which may reside on a cloud server environment. Unless a signal is received by the Receiver from Data Analytic Component 1250, all collected data may be sent at 10 minute intervals.

All collected Sensor data may be stored via Data Analytic Component 1250 and may be made available to users and applications via a fixed computer as well as mobile phones and tablets. Data visualization, storage, and analysis features may be implemented in Data Analytic Component 1250 and available to all platforms via an Application Programming Interface (API). Data Analytic Component 1250 may also have access to third party data streams such as peak power rates, weather forecasts, water district restrictions, etc. to further refine data presented to a user.

Based on sensor data and other information stored by Data Analytic Component 1250, various reports or analysis may be generated such as:
1) Suggesting upcoming irrigation schedule.
2) Current and historical conditions in the field.
3) Metrics indicative of irrigation efficiency and salinity management.
4) Metrics indicative of determined soil properties such as field capacity, water percolation rates, etc.
5) Alarms indicating conditions outside of preset limits.
6) Forward looking irrigation demands based on current conditions and future weather forecasts.
7) Plant stress indices (dependent on moisture and salinity levels).
8) System deployment metrics (missing Sensor packets, equipment health, hardware locations, battery levels, etc.)
9) Account management aspects such as authorized users, passwords, user configurations, etc.

Data Analytic Component 1250 may also support a mobile installation application that captures GPS locations, hardware serial numbers, and identifies which Sensors are located within receive distance of the Receivers. Data Analytic Component 1250 may also support a mobile installation application that provides client information, any additional information such as irrigation water quality data, soil maps, irrigation equipment type, etc.

During the growing season, a client may use System 1200 to monitor current soil moisture conditions and to schedule irrigation times and the amount of water to be applied. During irrigation, the Sensors may report data at a shorter interval allowing interactive control of the irrigation, such as terminating irrigation at a certain moisture threshold. Tracking the temperature and moisture conditions with the Sensors in System 1200 across the season may allow for identifying disease issues such as mold, leaf rot, as well as when weed germination may occur and when optimum planting times should occur. Salinity may be tracked via System 1200 and when salinity builds to levels that will impact plant health/yield, intense irrigation to flush salts below the root zone may be triggered and Sensor data may be used to monitor the efficacy of the flushing operation. At harvest, the map of yield may be compared to actual Sensor data to help highlight areas of low or high yield and modify future behavior to increase yield.

In locations such as greenhouses, grow operations, arboretums, interior planters, etc. the Receiver pickup coils used in System 1200 may be quite large and built into the floor, growing tables, or planter boxes and shelves. This may allow individual pots or planter boxes to have Sensors in them and when placed in these areas, Sensor data may be received to manage operations down to the single plant level if desired. Similarly, this approach may be implemented on roadways or in structures such as buildings, dams, and canals to monitor moisture, cement curing, or other important parameters.

In some embodiments, Data Analytic Component 1250 may also receive information relating to the amount of water supplied over time to an area being measured by a Sensor. For example, in an application where Sensors are embedded in a levee, Data Analytic Component 1250 may receive information indicating the water level or flow rate of water near each Sensor. In such an embodiment, Data Analytic Component 1250 may use information about the amount of water being applied to each Sensor to make predictions about future moisture levels or salinity. In further embodiments, Data Analytic Component 1250 may also utilize weather forecast information in making predictions about future moisture levels or salinity. In other embodiments, such as where the water being applied in the area of each sensor is controllable (e.g., an irrigation system), Data Analytic Component 1250 may use information about the amount of water that has been applied to an area around each Sensor and also weather forecast information to calculate irrigation schedules.

Figure 15:
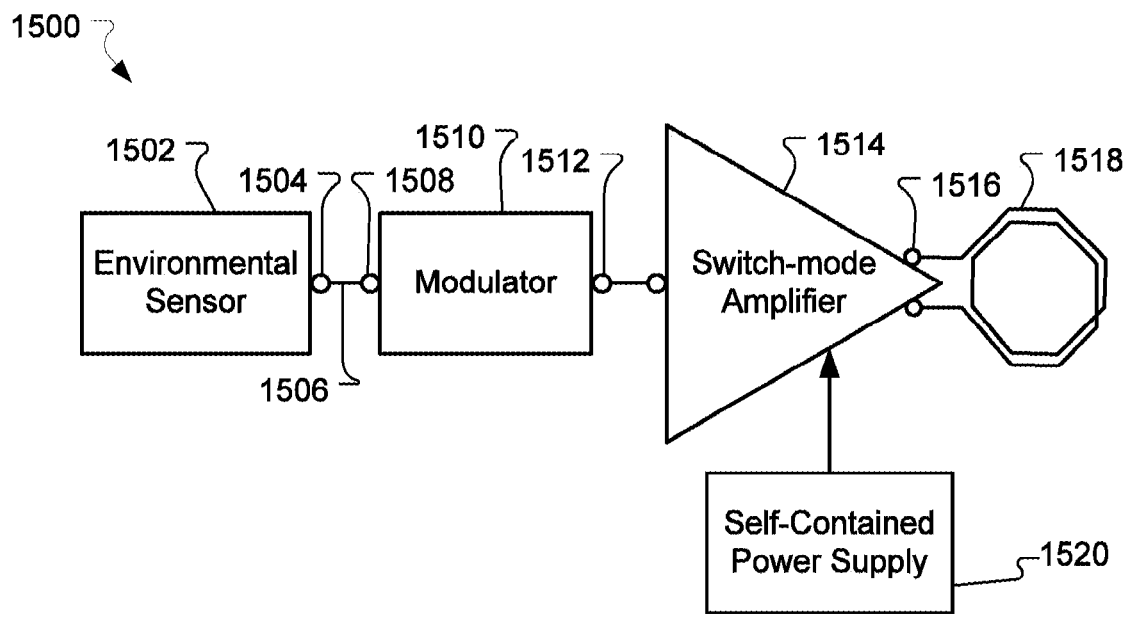
FIG. 15 is a diagram illustrating an embodiment of a telemetry system.

FIG. 15 illustrates an example of a telemetry System 1500 for obtaining environmental readings from within an electromagnetic-absorbing material (e.g., soil) which may be used in System 1200 (and include techniques described above). The telemetry system may include an Environmental Sensor 1502 having a Sensor Data Output 1504. The Environmental Sensor 1502 may provide sensing of at least one environmental condition within the Material 1622 to produce Sensor Data 1506 at the Sensor Data Output 1504. The Environmental Sensor 1502 may, for example, be a moisture sensor (providing moisture measurements), a temperature sensor (providing temperature measurements), a salinity sensor (providing salinity measurements), or another type of environmental sensor. More than one type of Environmental Sensor 1502 may be included to provide multiple types of measurements. The Environmental Sensor 1502 may be a commercially-available sensor or may be an improved sensor implemented using any of the techniques described above.

The environmental Sensor Data Output 1504 may be coupled to a Data Input 1508 of a Modulator 1510. The Modulator 1510 may encode the Sensor Data 1506 onto a carrier provided at a Signal Output 1512 of the Modulator 1510. The carrier may be a low-frequency signal below about 1705 kilohertz as described in further detail below.

A switch-mode Amplifier 1514 may be coupled to the Modulator 1510. The switch-mode Amplifier 1514 may amplify the carrier to provide an amplified signal at an Amplifier Output 1516, which may be coupled to a multi-turn Coil 1518. A self-contained Power Source 1520 may provide power for the amplifier (and any other desired components of the System 1500). The power source may be, for example, a battery, a fuel cell, a supercapacitor, or other suitable self-contained source of energy.

Figure 16:
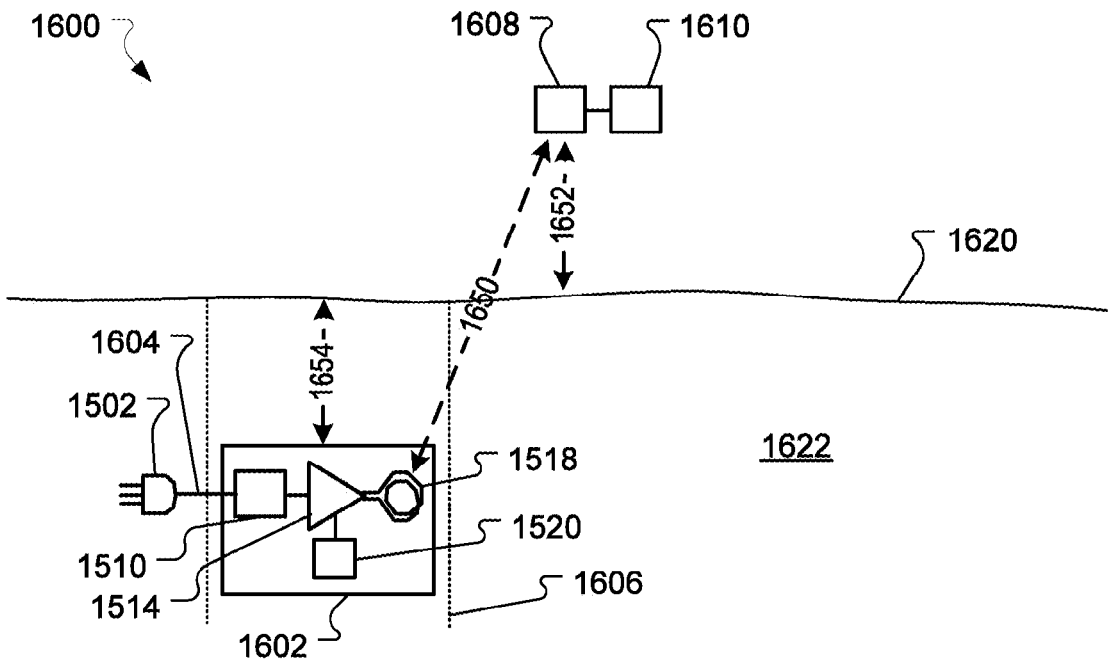
FIG. 16 is a diagram illustrating an example deployment of a telemetry system.

With respect to FIG. 16, an example deployment of a monitoring System 1600 employing the telemetry System 1500 is illustrated by which further example details may be understood. The monitoring System 1600 may be used for monitoring underground Material 1622 (e.g., soil) conditions (e.g., soil moisture for an agricultural operation). The telemetry System 1500 (e.g., Modulator 1510, Switch Mode Amplifier 1514, multi-turn Coil 1518 and self-contained Power Source 1520) may be packaged in a water-tight Enclosure 1602 and may be coupled to the environmental Sensor 1502 via wires or Cable 1604. The water-tight Enclosure 1602 may be installed into a Hole 1606 dug (drilled, bored, or otherwise formed) in the underground Material 1622, the environmental Sensor 1502 may be installed (e.g., inserted into undisturbed material) below a Surface 1620 of the Material 1622, and the Hole 1606 may be backfilled (e.g., refilled with the Material 1622 removed while making the hole). It can be understood that the water-tight enclosure can be further configured to inhibit ingress of fluids other than water therein.

The monitoring System 1600 may further include a Receiver Coil 1608 positioned outside the Material 1622 (e.g., above the Surface 1620). A Data Detector 1610 may be coupled to the receiver Coil 1608. A current driven into the multi-turn Coil 1518 by the switch-mode Amplifier 1514 may induce a current in the receiver Coil 1608 by mutual induction. From the current, the data encoded onto the carrier by Modulator 1510 may be detected. The detected data may be stored on a memory (e.g., a smart card; not shown) or communicated using other means (e.g., via a wired connection, a wireless connection, etc.; not shown) to a desired location (e.g., using techniques described above). As mentioned above, wirelessly communicating data from within the Material 1622 faces a number of challenges. Traditional propagating electromagnetic waves are generally not practical due to the high attenuation of the material. For example, a communication link that might operate through dry soil (relatively lower conductivity) may be unable to communicate when the soil becomes wet (higher conductivity) due to the increased attenuation. Moreover, typical wireless antenna structures are highly sensitive to the environment in which they are installed. For example, variation in the electromagnetic properties of the material (e.g., conductivity, permeability, permittivity) affect the performance (radiation resistance, impedance at resonance, radiation efficiency) of an antenna disposed within the material, which may cause antenna performance to vary, further impacting reliability of the communications link. Moreover, for commercially practical carrier frequencies (discussed further below), the wavelength at the carrier frequency within the material will be much larger than the antenna size, making it not feasible to rely on propagating electromagnetic waves.

Embodiments of the telemetry System 1500 may help to address these challenges by using near-field magnetic coupling. However, even using near-field magnetic coupling presents challenges. For example, the amount of coupling (mutual inductance) between the multi-turn Coil 1518 and the Receiver Coil 1608 drops off rapidly as the coils are separated. Accordingly, providing commercially useful communications ranges requires relatively high currents to be developed in the multi-turn coil. This is quite difficult in a power-constrained application (e.g., the self-contained Power Source 1520 is a battery). Moreover, the amount of coupling tends to be low when the coil diameter is small.

While longer range communication may be achieved by using a larger coil, the proportionately larger the enclosure and excavation must be. Using a multi-turn Coil 1518 allows for generating a higher magnetic field level, but at the expense of requiring a higher drive voltage, further impacting potential battery life. Even so, at commercially practical carrier frequencies, reasonable coil diameters are much smaller (e.g., less than 1/100th) than the wavelength of the carrier frequency within the material.

Using techniques described in further detail below, communication may be reliably achieved even when the multi-turn Coil 1518 is positioned within the Material 1622 at least 0.3 meters (1 foot) from the surface of the Material 1622 (shown as distance 1654) and the receiver Coil 1608 is positioned outside the Material 1622 at least 2 meters from the surface of the Material 1622 (shown as Distance 1652). In some embodiments, communications may be supported when the multi-turn Coil 1518 is separated by a distance (shown as Distance 1650) at least 3 meters from the receiver Coil 1608.

In accordance with some embodiments of the monitoring system 1600, the multi-turn Coil 1518 can having a diameter of less than about 0.3 meters (about 12 inches). In some embodiments, the multi-turn Coil 1518 may have a diameter of less than about 0.15 meters (about 6 inches). In some embodiments, the multi-turn Coil 1518 may have a number of turns between 10 and 100. With such sizes, packaging the multi-turn coil within an enclosure (e.g., enclosure 1602) suitable for burying or other field deployment becomes more practical.

With such a small coil size and the high-impedance (e.g., 500 ohms or greater) that results from the multi-turn nature of the multi-turn Coil 1518, a high driving voltage (e.g., 100 volts or greater) is used to provide a sufficiently high strength magnetic field to allow commercially useful communication ranges. However, a typical self-contained power source, such as a battery, may only provide relatively low voltages (e.g., less than 12 V, about 4.5 V, about 3 V, etc.). Efficiently developing high voltages from a low voltage source is another challenge.

Accordingly, a switched mode Amplifier 1514 may be used to address one or more of these challenges. The switch mode Amplifier 1514 may be designed to minimize voltage and/or current during the switching transients of the Amplifier 1514 (e.g., when the primary active device in the Amplifier 1514 is switching). The multi-turn Coil 1518 may have an impedance (at the carrier frequency) that forms a part of a load network of the Amplifier 1514. Additional reactive components (e.g., capacitors, inductors) may be used to tune the load network to form a resonant circuit at the carrier frequency. By maintaining a relatively good Q factor (e.g., greater than about 10) in the load network, the load network may also help to reduce harmonic components.

Figure 17:
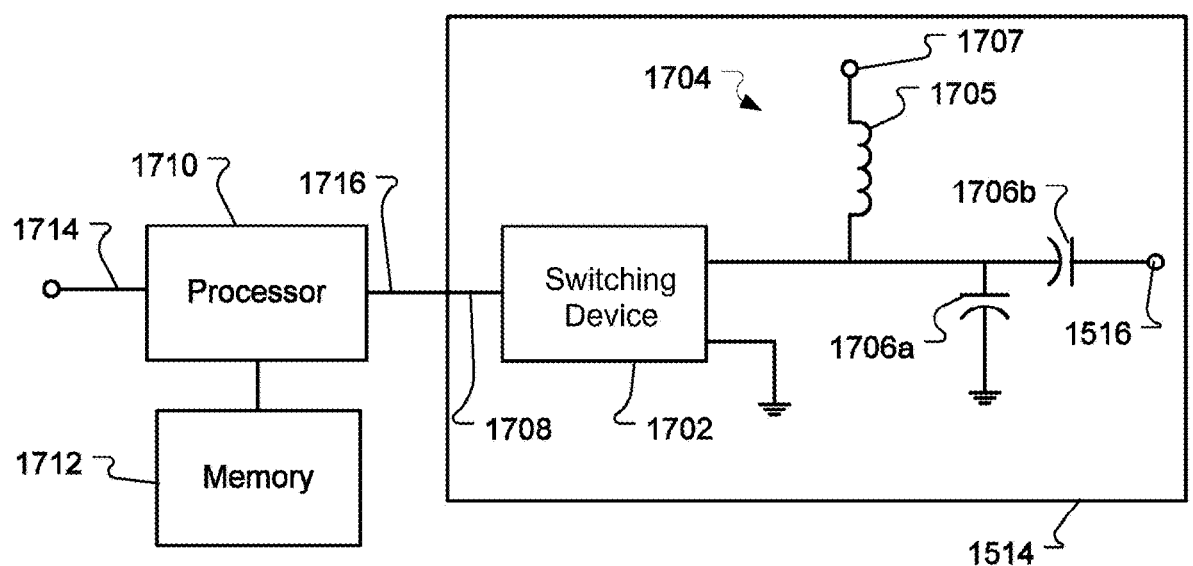
FIG. 17 is a diagram illustrating an example modulator coupled to an example switch-mode amplifier.

FIG. 17 illustrates an example of the switch-mode Amplifier 1514. The topology of the switch-mode Amplifier 1514 is similar to a "class E" amplifier, and in some embodiments, the switch-mode Amplifier 1514 may be a class E amplifier. The switch-mode Amplifier 1514 includes a Switching Device (e.g., a transistor) 1702 coupled to a Load Network 1704 (which includes the multi-turn Coil 1518, which although not shown in FIG. 17, may be connected to an Output 1516 of the switch-mode amplifier). The switching device 1702 can be referred to interchangeably herein as a switch device or switch. The load network may include an one or more circuit elements (e.g., Inductor 1705, Capacitor 1706a, and Capacitor 1706b, alone or in combination) to tune the load network as described above. Even though the switch-mode amplifier 1514 may be powered at Terminal 1707 by a relatively low voltage (e.g., from the self-contained power source 1520, as described above), the resulting voltages in the load network 1704 may be quite high (e.g., in excess of 100 volts), providing sufficient current flow (e.g., in excess of 100 milliamperes). In general, the switch-mode Amplifier 1514 may be designed to minimize voltage and/or current through the switching device 1702 when the switching device 1502 transitions between on and off states, thereby reducing power. The Carrier Input 1708 to the switch-mode Amplifier 1514 may be provided by a Digital Processor 1710 as described in further detail below.

The carrier frequency may impact both the efficiency of the switch-mode Amplifier 1514 as well as the communications range that may be achieved by the telemetry System 1500. In some embodiments, the switch-mode Amplifier 1514 may provide a power-conversion efficiency of at least 90%. On one hand, higher carrier frequency may allow for higher magnetic field strength for a given multi-turn Coil 1518 size (potentially allowing for longer range), but this may be offset by reduced efficiency of the amplifier and increased attenuation of the magnetic field by the material. Furthermore, for sufficiently high carrier frequencies (e.g., above 1705 kHz), field strength limits imposed by regulatory agencies may prohibit operation and deployment of devices or require special licenses to be obtained. On the other hand, while lower carrier frequency may result in less attenuation by the Material 1622, component values may become challenging (e.g., large inductors are needed which may be impractical) and coupling between the multi-turn coil 1518 and the receiver Coil 1608 may be greatly reduced, reducing communications range. Regulatory limits on radiated emissions may make operation at higher frequencies difficult. In contrast, at lower frequencies, regulatory limits are generally easier to meet, and accordingly, operation at lower frequencies may allow operation at higher field strengths, allowing for longer range. In some embodiments, the electric field produced by the multi-turn Coil 1508 may be less than a level of 24000/F volts per meter (V/m) when measured at a distance of 30 meters from the multi-turn coil 1508, wherein F is the carrier frequency in kilohertz (kHz). In some embodiments, the electric field may be less than a level of 2400/F V/m when measured at a distance of 300 meters.

As a result, operation below 1705 kHz may allow for unlicensed operation. More particularly, due to changes in regulatory limits below 490 kHz, operation below 490 kHz may allow for unlicensed operation using even higher field strength (resulting in longer range). Operation below 9 kHz may be challenging due to the low coupling (low induced voltage in the receiver coil), large component values, and some regulatory limits prohibiting some forms of communication at frequencies below 9 kHz. Accordingly, in some embodiments, the carrier frequency may be between about 9 kHz and about 1705 kHz. Operation above 50 kHz may allow for more useful communications range. Accordingly, in some embodiments, the carrier frequency may be between about 50 kHz and about 490 kHz.

With respect to the Modulator 1510, various techniques may be used to implement the modulator. As shown in FIG. 17, in one embodiment, the Modulator 1510 may be implemented using a Digital Processor 1710. The Digital Processor 1710 may have an Input Port 1712 that may provide a mechanism for obtaining Sensor Data 1506 from the environmental Sensor 1502 (not shown in FIG. 17). A Memory 1714 may be coupled to the processor and provide a non-transitory computer-readable media for storing instructions thereon for the processor. In some embodiments, the Digital Processor 1710 and Memory 1714 may be provided by a single integrated circuit. In alternative embodiments, instructions can be wirelessly transmitted to the telemetry system 1500. As an example, the receiver coil 1608 can transmit command signals containing instructions that are received by the multi-turn Coil 1518.

The instructions may, for example, comprise software for causing the Digital Processor 1710 to perform various functions for the telemetry System 1500 (e.g., sampling sensors, multiplexing several sensor measurements together, determining sampling intervals, time tagging measurements, etc.). In some embodiments, the instructions may cause the Digital Processor 1710 to generate a carrier in the form of a digital signal output from an Output Port 1716 of the Digital Processor 1710. Accordingly, the Digital Processor 1710 with instructions may provide a mechanism for encoding the Sensor Data 1506 onto a carrier. For example, the instructions may include a software module driven by a regular timing source (e.g., an interrupt, timing loop, and other techniques known to one of ordinary skill in the art) to generate a periodic signal with a desired frequency. For example, the carrier may be generated as a substantially square wave, which, as described above, may be converted by the switch-mode Amplifier 1514 into a substantially sinusoidal wave. The carrier output from the processor may not be precisely a square wave due to various factors including, but not limited to: limited slew rate of the input/output port, noise, and other factors known to those of ordinary skill in the art. Moreover, the resulting sinusoidal wave produced by the Amplifier 1514 may not be precisely sinusoidal due to various factors including, but not limited to, harmonic content, noise, and other factors known to those of ordinary skill in the art.

Information may be encoded onto the carrier by varying at least one parameter of the square wave. For example, the parameter may be the duty cycle (amplitude modulation), frequency (frequency modulation), phase (phase modulation) or combinations thereof. In some embodiments, the information may be encoded using on-off keying, which provides benefits in both simplicity and reduced power consumption. For example, a digital zero may be represented by a zero amplitude, and a digital one may be represented by the maximum amplitude. Accordingly, in some embodiments, the instructions for the Digital Processor 1710 may cause the Digital Processor 1710 to directly generate the on-off keyed carrier by outputting a square wave during intervals corresponding to a "one" and providing no output during intervals corresponding to a "zero."

In some embodiments, the Sensor Data 1506 may be encoded onto the carrier using an asynchronous communications protocol having a predetermined baud rate. For example, the baud rate may be between about 400 and about 2000 baud per second. Using an asynchronous communications protocol may provide for very efficient implementation (e.g., many processors include embedded serial communications ports that may be leveraged for this usage). Data may be transmitted in a periodic burst, and the amplifier may be turned off between bursts to save power. The telemetry System 1500 may use techniques described above in the context of System 1200, for example further minimizing power consumption using dynamic transmission schemes.

Beacon Mode

As mentioned earlier, the communication range of the multi-turn Coil 1518 can be limited, roughly 5 m to 20 m, depending on transmit power level, data rate, etc. Conventional hand held GPS receivers are only capable of positional accuracy to within about 5 m and this can be significantly degraded by topography, large nearby equipment, and if the observable GPS satellites are poorly positioned. Under some circumstances, this accuracy can be insufficient to allow a Receiver to be reliably placed close enough to the telemetry system 1500 to ensure reliable communication. In addition, conventional GPS will not allow one to conveniently retrieve a device containing the multi-turn Coil 1518 that is buried in the field if desired, as a 5 m typical accuracy would require a very impractical excavation effort. Furthermore, while precision differential GPS can be utilized over limited areas to achieve far better accuracy (down to 1 cm or so) over a limited area, this approach adds additional expense and equipment.

Additionally, existing sensing systems can employ a typical interval between sensor measurements and transmissions such as an hour or more, which can make using regular data transmission for location highly problematic. First, an interval of one hour between transmissions makes locating a transmitter device positioned below ground impractical, as it can require many hours to locate the device even with a rough GPS location. Second, the extended range is problematic as it does not provide a precise location—giving at best a relative location within 5 m or so, which is insufficient for recovering the transmitter devices positioned below ground or to establish that an above ground receiver is within reliable communication range across varying environmental factors.

These two limitations can be overcome by using transmissions according to a beacon mode that sends one or more signals of varying power levels at a frequent interval. The lower power levels can allow much more precise location (e.g., down to as low as 10 cm or better) and the more frequent signals can allow for a quick determination of location once within the general area. The frequent signals can require very efficient battery utilization as it is desirable for the below ground unit to have a lifetime of 5+ years. Simple beacon routines that can operate autonomously of a processor are also desirable to conserve battery power and offer additional flexibility.

A "Beacon Mode" according to embodiments of the present disclosure can be implemented by the telemetry system 1500 to allow an above ground Receiver to locate the telemetry system 1500 to within 10 cm or so by utilizing a very low power location signal to be sent periodically by the telemetry system 1500 that can be received by the above ground Receiver. The low power location signal can be used to determine where to install the above ground Receiver in a fixed, non-mobile application, to excavate the telemetry system 1500, if desired, and/or assist in the implementation of a mobile above ground transmitter/receiver (MAGTR) applications.

As discussed below, the Amplifier 1514 of the telemetry system 1500 can be configured to cause the coil 1518 to send periodic wireless signals, referred to herein as beacon signals, that can be employed to provide relative range information between a receiver outside of an electromagnetic absorbing material (e.g., 1622) and telemetry system 1500, allowing one to quickly locate the telemetry system 1500. In practice, one can use conventional GPS (such as on a smart phone) to get within the general area of the telemetry system 1500, and then use the Beacon Mode transmission to quickly fix in on a precise location, greatly simplifying and expediting practical field implantation of the telemetry system 1500.

Referring to the amplifier 1514 of the telemetry system 1500, a beacon signal can be generated by controlling the switching device 1702. As an example, during ordinary data transmission, the switch 1702 can be turned on/off at a predetermined switching frequency to generate a sinusoidal signal across the coil 1518. The predetermined frequency is the carrier frequency of the sinusoidal signal. In an embodiment, the switching frequency can be approximately equal to a resonant frequency of the resonant circuit formed by the load network 1704 and the coil 1518. As an example, the switching frequency can be about 174 kHz, generating a sinusoidal 174 kHz signal of hundreds of volts across the coil 1518. An on/off key (OOK) can be implemented, where a "1" can be sent by a 1 ms duration of the 174 kHz on/off of the switch 1702. A "0" can be sent by a 1 ms period of the switch 1702 being kept off. A receiver can convert a received weak voltage across the receiver coil 1608 into a logic input to Data Detector 1610. The received voltage can be measured to provide a measurement of the amplitude of the beacon signal.

Discussed below are two approaches for generating the beacon signals(s) during the beacon mode: 1) a short train of 174 kHz for on/off control of, for example, the switch 1702 in FIG. 17, which will typically be much shorter than the current 1 mS train time when sending data, and 2) a single, switch closure of variable duration (e.g., a predetermined time duration), also referred to herein as "hammering." Both of these features rely upon the behavior of the resonant structure in the transmitter (which includes the coil 1518), which does not turn on immediately at maximum strength at the start of the switch closure train, but rather ramps up.

The beacon signal can be generated with operating parameters (e.g., frequency, amplitude, number, interval, etc.) in accordance with instructions received by the switch-mode Amplifier 1714. In one aspect, the instructions can be stored in a memory device (e.g., Memory 1712) and provided to the telemetry System 1500 (e.g., Processor 1710). In alternative embodiments the instructions can be transmitted from the Receiver in the form of wireless command signals and received by the telemetry System 1500 (e.g., the multi-turn coil 1518). The command signals can be decoded by the Processor 1710 to obtain the instructions.

This can be understood by analogy to pushing a child on a swing with a series of pushes. With successive pushes, the amplitude of the swing slowly builds up. Continuing the analogy, the swing needs to be pushed at the right time (in this case, the right frequency) or the amplitude doesn't build up much. Similarly, in the second approach using a single pulse (hammering), the energy from the pulse starts the transmitter oscillating at the natural frequency (e.g., 174 kHz) for a period of time as it decays from losses in the circuit. Additionally, the longer the pulse, the more energy is imparted and the stronger the oscillation. An appropriate analogy is striking a bell with a hammer, whereupon it will ring at the natural frequency. A harder hit (or in this case longer pulse) generates a louder sound, but it doesn't change the tone.

It can be understood that in both beacon approaches, the amplitude of the oscillation on the coil 1518 (and hence the transmitted strength of the beacon signal) can be made much smaller and the duration can be much shorter. These combine to produce an energy requirement for generating the beacon signal that is much smaller than typically used to send data, helping to converse battery life. The lower transmit intensity reduces the reception range, which can provide more accurate localization of the telemetry system 1500 (e.g., enclosure 1602). For example if the beacon signal range is 1 m, detection of the beacon signal by the Receiver indicates that the Receiver is within 1 m of the coil 1518 and enclosure 1602. In contrast, using a typical transmission strength for detection of the coil 1518 and enclosure 1602 would only identify the enclosure's location to within 5-20 m.

The amplitude (strength) of the beacon signal received at the receiver can be adjusted in a variety of ways. In one aspect, the amplitude of the beacon signal can be increased by increasing the input voltage at point 1707 in FIG. 17. Conversely, the amplitude of the beacon signal can be decreased by decreasing the input voltage.

In another aspect, the amplitude (strength) of the beacon signal received at the receiver can be adjusted by shifting a frequency of the beacon signal. As discussed above, the switching frequency of the switching device 1702 controls the frequency of the beacon signal. In general, keeping other factors constant, the amplitude of the transmitted beacon signal increases as the frequency of the beacon signal approaches the resonant frequency of the resonant circuit formed by the load network 1704 and the coil 1518. Similarly, keeping other factors constant, the amplitude of the received beacon signal increases as the frequency of the transmitted beacon signal approaches a resonant frequency of the receiver. As discussed above, thus, the switching device 1702 can control the frequency of the beacon signal. Thus, the switching device 1702 can control the amplitude of the beacon signal received by the receiver by shifting the frequency of the beacon signal. Adjustment of the amplitude of the beacon signal can be performed alone or in combination with short pulse trains at the resonant frequency or a single pulse—"hammering" discussed above.

While an operating frequency of 174 kHz is discussed above, embodiments of the operating frequency can be different. In general, the operating frequency can be selected to match the frequency of operation of the transmitter. As an example, the operating frequency can be selected between about 9 kHz to about 1705 kHz.

(a) Series of Beacon Strengths

In further embodiments, the beacon signal can be varied in amplitude (strength). As discussed below, this manner of transmitting in the beacon mode can greatly assist in locating the coil 1518 and enclosure 1602.

In one aspect, three beacon signals of varying transmit strengths can be sent. As an example, the three beacon signals can be employed every second, staggered in time with varying strengths and ranges: High—5 m, Medium—2 m, Low—1 m. One exemplary timing of the beacon signals can be implemented as follows: at t=0s, generate High beacon, at t=0+10 ms, generate Medium beacon, at t=0+20 ms, generate Low beacon and at t=0+1000 ms and the process can repeat. This can be repeated as necessary to generate three closely spaced beacons of varying strength every 1 s. The interval between the beacons can be beneficial to allow the previous beacon oscillation in the transmitter to fully decay before the next beacon signal starts. While generation of three beacon signals are discussed above, it can be understood that embodiments of the telemetry System can generate different numbers of beacon signals having independently selected amplitude and duration between adjacent beacon signals.

In another aspect, a first beacon mode can employ a first, single beacon signal of high amplitude. Detection of this first beacon signal by the Receiver can identify the position of the telemetry System 1500 within a first distance. Subsequently, a second beacon mode can employ a plurality of second beacon signals with amplitude less than the first beacon signal (e.g., the high, medium, and low beacon signals discussed above). The lower amplitude second beacon signals are detectable over a smaller distance than the higher amplitude first beacon signal. That is to say, using beacon signals of smaller amplitude in sequence can provide progressively finer resolution to identify the location of the telemetry System 1500.

The advantage of this approach is that, with an appropriate Receiver above ground, a given area can be quickly traversed to find the telemetry system 1500 and enclosure 1602 below ground. In an exemplary use case, the Receiver can be incorporated into a portable computing device (e.g., a smartphone or tablet). A user can execute an app on the portable computing device and select a particular enclosure 1602 they would like to locate. From the cloud, the app can pull down the GPS location and guide the user to the rough location (e.g., within about 10 m). The user then triggers to enter a "Hunt" mode to detect the beacon signal.

The detected beacon signal can be employed to determine an approximate distance (relative proximity) of the Receiver to the telemetry system 1500. As an example, the portable computing device can measure the amplitude of a received beacon signal. The portable computing device can further generate feedback when one or more beacon signals can be detected. As an example, a beacon signal can be detected by the portable computing device when the measured amplitude of the beacon signal is greater than or equal to a threshold amplitude.

The above ground Receiver can generate a feedback to the user to provide an indication of the proximity of the Receiver to the telemetry system 1500. In one aspect, the feedback can be audio feedback. As an example, the Receiver can be in communication with a speaker. The speaker can generate audible noises during a predetermined time duration representing proximity of the Receiver to the telemetry system 1500 (e.g., no beep, beep once, beep twice, beep three times per second). In another aspect, the feedback can be visual feedback. As an example, the Receiver can be in communication with a flash of light (e.g., an LED). The light can turn on and off during a predetermined time duration to represent proximity of the Receiver to the telemetry system 1500 (e.g., no flash, flash once, flash twice, flash three times per second). The more beeps or flashes generated, the closer the Receiver is to the enclosure 1602 containing the telemetry system 1500. In a further aspect, the proximity of the Receiver to the telemetry system 1500 can be displayed by the portable computing device.

The distance or proximity of the Receiver to the telemetry system 1500 system can be determined in a variety of ways. In one example, the amplitude of the beacon signal can be correlated to a distance separating the Receiver and the telemetry system 1500 by a lookup table maintained by the Receiver. This provides intuitive feedback to the user. With a rapid beacon cycle, in this example 1s, the user can move quickly though a search radius around the nominal GPS location to locate the unit to about 1 m.

(b) Precise Location Through Coil Rotation

While locating the telemetry system 1500 and enclosure 1602 to within 1 m can be sufficient for monitoring and forwarding on the reported data, it can be too crude for effectively locating the telemetry system 1500 and enclosure 1602 for removal. Notably, locating the telemetry system 1500 and enclosure 1602 within a 1 m radius could require digging a hole 2 m in diameter.

Figure 18B:
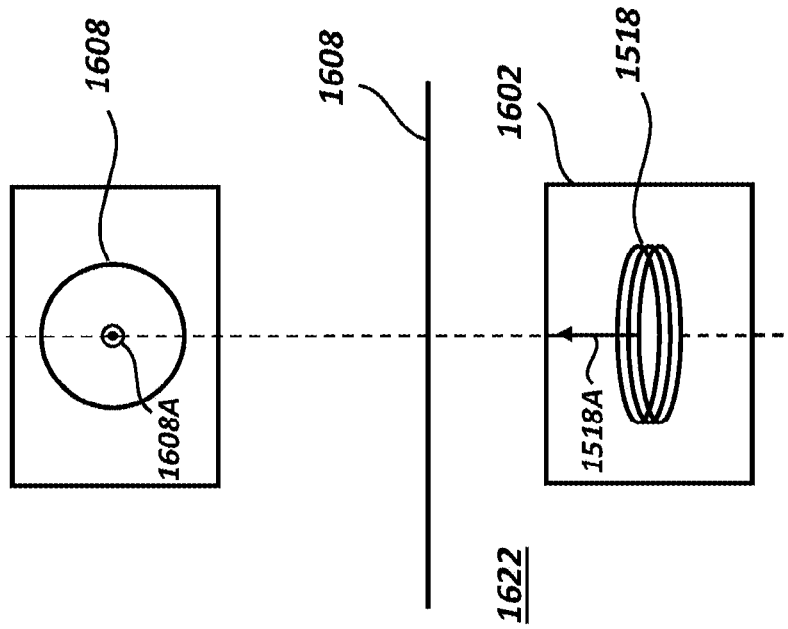
FIGS. 18A-18B are diagrams illustrating use of coil rotation for determining location in a beacon mode of operation. (A) Maximum received signal geometry. (B) Minimum (null) received signal geometry.
Figure 18A:
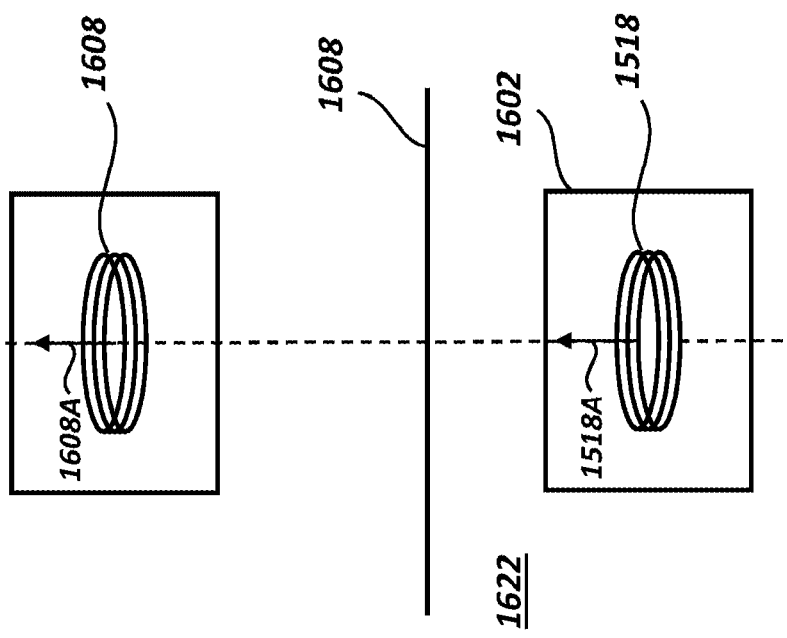

To address this issue and effectively to locate the enclosure 1602 down to approximately 0.1 m, asymmetric transmit/receive geometry can be exploited (see FIG. 18A-18B).

The received amplitude (strength) of the transmitted beacon signal is highest when the two coils (e.g., transmit coil 1518 and receiver coil 1608) face each other and their respective coil axes (1518A and 1608A) are parallel. The received amplitude (strength) of the transmitted beacon signal is at a minimum (null) when the coils 1518 and 1608 are directly above each other and their respective coil axes (1518A and 1608A) are orthogonal. In a typical install geometry with the axis 1518A of the transmitter coil 1518 can be fixed in place, orthogonal to the soil surface 1608, with the axis 1608A of the receiver coil 1608 oriented parallel to the soil surface 1608 (FIG. 18B). To locate the telemetry system 1500, a user can move the above ground Receiver (e.g., portable computing device) laterally (e.g., horizontally) with respect to the surface of the Material 1622. That is, the distance 1620 can be maintained approximately constant during movement of the Receiver. Thus, the null condition occurs when the receiver coil 1608 is directly over the transmitter coil 1518. With this configuration, it is possible to locate the telemetry system 1500 and enclosure 1602 to within about 10 cm or better by noting when the amplitude of the weakest beacon signal is less than the predetermined amplitude threshold, while the medium and/or high beacon signals remain above the predetermined amplitude threshold.

(c) Autonomous Beacon

Figure 19:
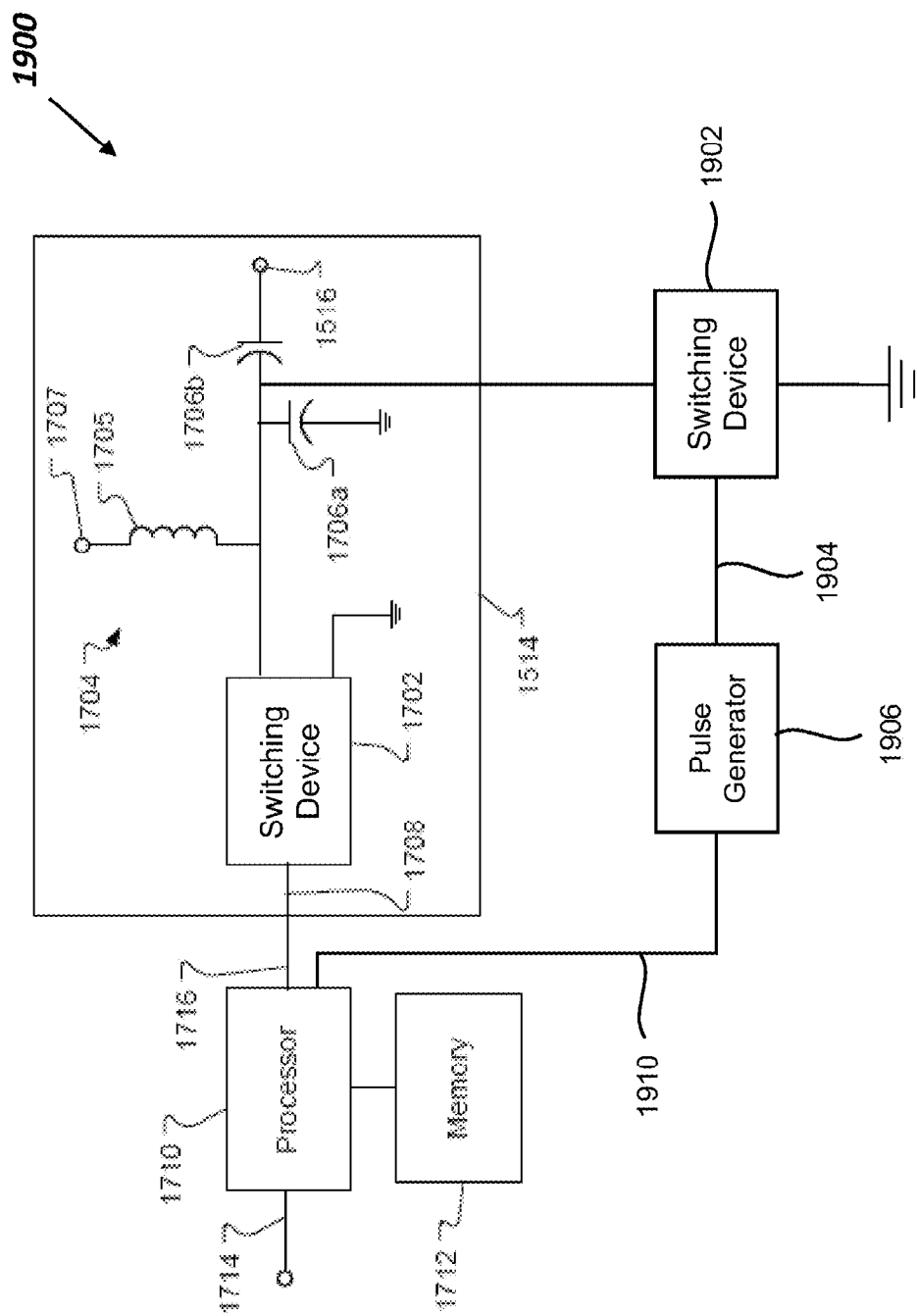
FIG. 19 is a circuit diagram modifying the circuit of FIG. 17 to support operation of an autonomous beacon.

When using a 174 kHz pulse train to generate a beacon signal, precise frequency tolerance (e.g., 1% or better) can be required. This tolerance can be difficult to achieve without using a crystal based processor. However, the hammering approach to generating beacon signals can easily be implemented without a processor, an approximate interval can be required between the closure of the switch 1702 and rough durations of the switch closed times. This can be accomplished, for example by using a positive going pulse generator that generates a 2 µs high pulse every second that is used to control a transistor switch. These pulse generators can be extremely low power (on the order of 1 uA @ 3.3V), which is much less than what would be used for typical based solution. This can operate in conjunction with the processor 1710 as shown diagrammatically in FIG. 19. In this implantation, a Pulse Generator 1906 and a Switching Device 1902 are added to the circuit of FIG. 17 to provide circuit 1900 illustrated in FIG. 19. The switching device 1902 is in communication with the pulse generator via line 1904. The switch device 1902 is further in communication with the load network 1704. The switching device 1902 can be referred to interchangeably herein as a switch device or switch.

The pulse generator is used to control the switching device 1902 to generate a beacon pulse with no interaction from the processor 1710 other than output 1910 that can be used to disable the beacon pulse during actual data transmit. That is, the switching deice 1702 is maintained in the off state. As an example, the pulse generator 1906 can generate a beacon pulse (e.g., a high voltage) to the switch device 1902 for a predetermined time via the line 1904. In response to receipt of the beacon pulse, the switch device 1902 can be placed in the on state and the multi-turn Coil 1518 can generate the beacon signal. The duration of the generated beacon signal can be approximately the same as the duration of the beacon pulse generated by the pulse generator 1906.

In addition to embodiments described using software, various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination thereof. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Various modifications to these embodiments will be readily apparent to those skilled in the art, and the generic principles described herein can be applied to other embodiments without departing from the spirit or scope of the invention. Thus, it is to be understood that the description and drawings presented herein represent presently preferred embodiments and are therefore representative of the subject matter which is broadly contemplated by the present invention. It is further understood that the scope of the present invention fully encompasses other embodiments that may become obvious to those skilled in the art and that the scope is accordingly not limited.

While various embodiments have been described above, it should be understood that they have been presented by way of example only, and not of limitation. The breadth and scope should not be limited by any of the above-described exemplary embodiments. For the purpose of clarity, technical material that is known in the technical fields related to the invention has not been described in detail so that the invention is not unnecessarily obscured. Where this document refers to technologies that would be apparent or known to one of ordinary skill in the art, such technologies encompass those apparent or known to the skilled artisan now or at any time in the future. In addition, the described embodiments are not restricted to the illustrated example architectures or configurations, but the desired features can be implemented using a variety of alternative architectures and configurations. As will become apparent to one of ordinary skill in the art after reading this document, the illustrated embodiments and their various alternatives can be implemented without confinement to the illustrated example. One of ordinary skill in the art would also understand how alternative functional, logical or physical partitioning and configurations could be utilized to implement the desired features of the described embodiments.

The singular forms "a," "an," and "the" include plural referents unless the context clearly dictates otherwise; although items, elements, or components may be described or claimed in the singular, the plural is contemplated to be within the scope thereof unless limitation to the singular is explicitly stated. The presence of broadening words and phrases such as "one or more," "at least," "but not limited to," or other like phrases in some instances shall not be read to mean that the narrower case is intended or required in instances where such broadening phrases may be absent. The term "plurality" means two or more. The order of the steps of disclosed processes may be altered unless specified otherwise or otherwise clear from context. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, or processing cores configured to process data, such as computer program instructions. The term "coupled to" and the like used herein includes direct coupling and/or indirect coupling between items via an intervening item as will be understood by a person of ordinary skill in the art. For example, electronic elements may be coupled by intermediary circuitry that adjusts voltage, current, power, impedance, or other properties of the electronic signal passed between the items. The terms "about," "substantially," and "approximately" and the like used herein provides an industry-accepted tolerance for its corresponding term and/or relativity between item, such as for example, manufacturing process limitations and measurement accuracy. The term "comprising," used herein means "including, but not necessarily limited to"; it specifically indicates open-ended inclusion or membership in the so-described combination, group, series, and the like.

EXEMPLARY EMBODIMENTS

The following concise examples of various embodiments of the invention are now be provided, the examples disclosing combinations of features described previously above.

Example 1. A telemetry system for obtaining environmental readings from within an electromagnetic-absorbing material, the system comprising:
  an environmental sensor having a sensor data output;
  a modulator having a data input coupled to the sensor data output and a signal output, wherein the modulator encodes data received at the data input onto a carrier produced at the signal output, and wherein the carrier has a carrier frequency between about 9 kHz and about 1705 kHz;
  a switch-mode amplifier coupled to the signal output and having an amplifier output;
  a multi-turn coil coupled to the amplifier output, wherein the multi-turn coil has a diameter of less than about 0.3 meter, and wherein the multi-turn coil has a reactance at the carrier frequency that forms a part of a frequency-dependent load network coupled to the amplifier; and
  a self-contained power source coupled to the switch-mode amplifier.

Example 2. The telemetry system of Example 1, wherein the modulator comprises a digital processor configured to generate the carrier.

Example 3. The telemetry system of Example 2, wherein the digital processor outputs the carrier as a substantially square wave, and wherein the amplifier converts the substantially square wave into a substantially sinusoidal wave.

Example 4. The telemetry system of any of Examples 1-3, wherein the modulator encodes the data received at the data input onto the carrier using on-off keying.

Example 5. The telemetry system of any of Examples 1-4, wherein the switch-mode amplifier is a class-E amplifier.

Example 6. The telemetry system of any of Examples 1-5, further comprising:
  a receiver coil positioned outside the material; and
  a data detector coupled to the receiver coil; and
  wherein the receiver coil is separated from the multi-turn coil by at least 2 meters.

Example 7. The telemetry system of Example 6, wherein the multi-turn coil is positioned at least 0.6 meters from a surface of the material, and the receiver coil is positioned outside the material and at least 2 meters from the surface of the material.

Example 8. The telemetry system of Example 6, wherein the multi-turn coil is positioned at least 0.3 meters from a surface of the material, and the receiver coil is positioned outside the material and at least 3 meters from the surface of the material.

Example 9. The telemetry system of Example 6, wherein the receiver coil is mounted on a moving structure.

Example 10. The telemetry system of any of Examples 1-9, wherein the self-contained power source is one or more of: a battery, a fuel cell, a super capacitor.

Example 11. The telemetry system of any of Examples 1-9, wherein the modulator, the amplifier, the multi-turn coil, and the power source are packaged within a water-tight enclosure.

Example 12. A method of telemetering from within an electromagnetic-absorbing material, the method comprising:
  sensing an environmental condition within the material to produce sensor data; encoding the sensor data onto a carrier having a carrier frequency between about 9 kHz and about 1705 kHz;
  amplifying the carrier using a switch-mode amplifier to produce an amplified signal, wherein the switch-mode amplifier is powered from a self-contained power source; and
  coupling the amplified signal into a multi-turn coil, wherein the multi-turn coil has a diameter of less than about 0.3 meter, and wherein the multi-turn coil has a reactance at the carrier frequency that forms a part of a frequency-dependent load network coupled to the amplifier.

Example 13. The method of Example 12, wherein the encoding the sensor data onto a carrier comprises:
generating a substantially square wave;
modifying at least one parameter of the square wave, wherein the at least one parameter is selected from the group consisting of: amplitude, phase, frequency, and combinations thereof; and
wherein the amplifier converts the substantially square wave into a substantially sinusoidal wave.

Example 14. The method of any of Examples 12-13, wherein the encoding the sensor data onto a carrier further comprises: encoding the data using a serial asynchronous communications protocol having a predetermined baud rate.

Example 15. The method of Example 14, wherein the baud rate is between about 500 and about 2000 baud per second.

Example 16. The method of any of Examples 12-15, further comprising:
positioning a receiver coil outside the material; and
detecting the data using current induced in the receiver coil by mutual induction with the multi-turn coil.

Example 17. The method of any of Examples 12-15, further comprising:
positioning the receiver coil at least 2 meters from a surface of the material, and wherein the multi-turn coil is positioned at least 0.3 meters from a surface of the material.

Example 18. The method of any of Examples 12-17, wherein the data is transmitted in a periodic burst, and the amplifier is turned off between bursts.

Example 19. The method of Example 18, wherein an interval between bursts is varied using a dynamic sensor data transmission scheme.

Example 20. A telemetry system for obtaining environmental readings from within an electromagnetic-absorbing material, the system comprising:
a means for obtaining sensor data;
a means for encoding the sensor data onto a carrier, wherein the carrier has a carrier frequency between about 9 kHz and about 1705 kHz;
a means for amplifying the carrier having a power-conversion efficiency of at least 90 percent;
a multi-turn coil coupled to the means for amplifying, wherein the multi-turn coil has a diameter of less than about 0.3 meter; and
a self-contained power source coupled to the means for amplifying.

Example 21. Any preceding example, wherein the carrier frequency is between about 50 kHz and about 490 kHz.

Example 22. Any preceding example, wherein the carrier frequency has a wavelength within the material, and the wavelength is much larger than the diameter of the multi-turn coil.

Example 23. Any preceding example, wherein the material is one or more of: soil, water, rock, concrete, and combinations thereof.

Example 24. Any preceding example, wherein the material has a varying electromagnetic parameter selected from the group consisting of: permittivity, permeability, conductivity, and combinations thereof.

Example 25. Any preceding example, wherein the sensor data comprises one or more of: moisture measurement, temperature measurements, and salinity measurements.

Example 26. Any preceding example, wherein an electric field produced by the multi-turn coil is less than a level of about 24000/F volts/meter when measured at a distance of 30 meters from the multi-turn coil, wherein F is the carrier frequency in kilohertz.

Example 27. Any preceding example, wherein an electric field produced by the multi-turn coil is less than a level of about 2400/F volts/meter when measured at a distance of 300 meters from the multi-turn coil, wherein F is the carrier frequency in kilohertz.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be a Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method of locating a sensor, comprising:
   placing an environmental sensor within an electromagnetic absorbing material, the environmental sensor being configured to sense at least one environmental condition of the electromagnetic-absorbing material and to output sensor data representing the at least one environmental condition;
   providing a modulator in communication with the environmental sensor, wherein the modulator is configured to encode the sensor data onto a carrier at a predetermined carrier frequency;
   providing a switch-mode amplifier in communication with the signal output and a first multi-turn coil, wherein the switch mode amplifier comprises:
   a first switching device configured to transition between an on state and an off state;
   a load network coupled to the first switching device, the load network including a terminal configured to receive an input voltage and the first multi-turn coil, the inductance and capacitance of the load network being tunable to form a resonant circuit at the predetermined carrier frequency;
   generating, by the first multi-turn coil, a beacon signal, wherein an amplitude of the beacon signal is adjustable;
   receiving, by a second multi-turn coil of a receiver positioned outside of the electromagnetic-absorbing material, the beacon signal;
   measuring the amplitude of the received beacon signal; and
   determining a location of the environmental sensor based upon the measured amplitude of the beacon signal.

2. The method of claim 1, wherein generating the beacon signal comprises generating a single beacon signal by placing the first switching device in the on position for a predetermined time duration.

3. The method of claim 1, wherein generating the beacon signal comprises generating a plurality of beacon signals by transitioning the first switching device between the on state and off state for each beacon signal.

4. The method of claim 1, wherein the amplitude of the beacon signal is adjusted by changing the magnitude of the input voltage.

5. The method of claim 1, wherein the amplitude of the generated beacon signal is adjusted by shifting a frequency of the beacon signal with respect to a resonant frequency of the resonant circuit.

6. The method of claim 1 further comprising receiving, by the first multi-turn coil, a command signal operative to adjust the amplitude of the beacon signal.

7. The method of claim 1, wherein the first multi-turn coil generates the beacon signal when the first switching device is placed in the on state.

8. The method of claim 1, further comprising:
provide a pulse generator in communication with a second switching device, the second switch device being further in communication with the load network;
generating, by the pulse generator, a beacon pulse; and
placing the second switching device in an on state during receipt of the beacon signal;
wherein the first multi-turn coil generates the beacon signal when the second switching device is placed in the on state; and
wherein the first switching device is placed in the off state during generation of the beacon pulse and the second beacon signal.

9. The method of claim 1, wherein the method further comprises:
generating a first beacon signal having a first amplitude and a first duration;
generating a second beacon signal having a second amplitude and a second duration; and
generating a third beacon signal having a third amplitude and a third duration;
wherein the first amplitude is greater than the second and third amplitudes and the second amplitude is greater than the third amplitude; and
wherein the first duration is less than the second and third durations and the second duration is less than the third duration.

10. The method of claim 9 wherein an axis of the first multi-turn coil is oriented orthogonally to a surface of the electromagnetic-absorbing material, and wherein the method further comprises:
orienting the receiver such that an axis of the second multi-turn coil is approximately perpendicular to the surface of the electromagnetic-absorbing material;
moving the receiver with respect to the first multi-turn coil while maintaining an approximately constant distance between the receiver and the surface of the electromagnetic-absorbing material; and
identifying the location of the environmental sensor as the location where the amplitude of the third beacon signal is less than a predetermined amplitude threshold and the amplitude of at least one of the first and second beacon signals is greater than or equal to the predetermined amplitude threshold.

11. The method of claim 9, further comprising determining a distance between the receiver and the environmental sensor based upon the measured amplitude of at least one of the first, second, or third beacon signals.

12. The method of claim 9, further comprising providing, by an audio or visual device, an indication of the distance between the Receiver and the environmental sensor.

13. The method of claim 1, wherein the predetermined carrier frequency is selected from about 9 kHz to about 1705 kHz.

14. The method of claim 13, wherein the predetermined carrier frequency is selected from about 50 kHz to about 490 kHz.

15. The method of claim 1, wherein the first multi-turn coil has a diameter of less than 0.3 meter.

16. The method of claim 1, wherein the switch-mode amplifier is a class-E amplifier.

* * * * *